United States Patent
Takahashi et al.

(10) Patent No.: US 9,512,070 B2
(45) Date of Patent: Dec. 6, 2016

(54) METHOD FOR PRODUCING COMPOUND CONTAINING BIS (PERFLUOROALKYLSULFONYL) METHYL GROUP AND SALT THEREOF, AND SOLID ELECTROLYTE MEMBRANE PRODUCED USING SAME

(71) Applicant: Central Glass Company, Limited, Ube-shi, Yamaguchi (JP)

(72) Inventors: Arata Takahashi, Tokyo (JP); Katsutoshi Suzuki, Hino (JP); Haruhiko Komoriya, Saitama (JP); Toru Tanaka, Fujimi (JP); Saori Itabashi, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/430,693

(22) PCT Filed: Sep. 24, 2013

(86) PCT No.: PCT/JP2013/075700
§ 371 (c)(1),
(2) Date: Mar. 24, 2015

(87) PCT Pub. No.: WO2014/050814
PCT Pub. Date: Apr. 3, 2014

(65) Prior Publication Data
US 2015/0266816 A1    Sep. 24, 2015

(30) Foreign Application Priority Data

Sep. 25, 2012 (JP) ................. 2012-210926
Sep. 19, 2013 (JP) ................. 2013-194615

(51) Int. Cl.
| | |
|---|---|
| C07C 315/04 | (2006.01) |
| C08G 61/08 | (2006.01) |
| H01M 8/10 | (2016.01) |
| H01M 8/04 | (2016.01) |
| B01J 39/20 | (2006.01) |
| C07C 317/04 | (2006.01) |
| C07C 317/06 | (2006.01) |
| C07C 317/10 | (2006.01) |
| C08F 132/08 | (2006.01) |

(52) U.S. Cl.
CPC .............. *C07C 315/04* (2013.01); *B01J 39/20* (2013.01); *C07C 317/04* (2013.01); *C07C 317/06* (2013.01); *C07C 317/10* (2013.01); *C08F 132/08* (2013.01); *C08G 61/08* (2013.01); *H01M 8/04197* (2016.02); *H01M 8/1011* (2013.01); *H01M 8/1027* (2013.01); *H01M 8/1032* (2013.01); *H01M 8/1039* (2013.01); *C07C 2101/14* (2013.01); *C07C 2102/42* (2013.01); *C08G 2261/146* (2013.01); *C08G 2261/1452* (2013.01); *C08G 2261/418* (2013.01); *H01M 2008/1095* (2013.01); *H01M 2300/0082* (2013.01); *Y02E 60/523* (2013.01)

(58) Field of Classification Search
CPC . C07C 315/04; C07C 317/04; C07C 317/06; C07C 317/10; C08G 61/08; H01M 8/1011; H01M 8/1032; H01M 8/04261; B01J 39/20; C08F 132/08
USPC ....................................................... 521/27
See application file for complete search history.

(56) References Cited

U.S. PATENT DOCUMENTS

| | | | |
|---|---|---|---|
| 3,586,616 A * | 6/1971 | Kropp | C08F 4/00 502/155 |
| 3,932,526 A | 1/1976 | Koshar | |
| 3,962,346 A | 6/1976 | Barber, Jr. et al. | |
| 4,053,519 A | 10/1977 | Koshar et al. | |
| 7,026,409 B2 | 4/2006 | Ishihara et al. | |
| 2003/0023001 A1 | 1/2003 | Kerr et al. | |
| 2011/0207900 A1 | 8/2011 | Yi et al. | |
| 2012/0301811 A1 | 11/2012 | Suzuki et al. | |
| 2013/0189220 A1 | 7/2013 | Komoriya et al. | |
| 2014/0066659 A1 * | 3/2014 | Taguchi | B01J 31/0224 564/440 |

FOREIGN PATENT DOCUMENTS

| | | | | |
|---|---|---|---|---|
| JP | 2002-338539 A | 11/2002 | | |
| JP | 2011-192640 A | 9/2011 | | |
| JP | 2012-508278 A | 4/2012 | | |
| JP | WO 2012081488 A1 * | 6/2012 | .......... | B01J 31/0224 |
| JP | 2012-126688 A | 7/2012 | | |
| WO | WO 2012/043619 A1 | 4/2012 | | |
| WO | WO 2012/081488 A1 | 6/2012 | | |

OTHER PUBLICATIONS

A. Hasegawa et al., "Facile Synthesis of Aryl—and Alkyl-bis(trifluoromethylsulfonyl)methanes," The Chemical Society of Japan, Bull. Chem. Soc. Jpn., vol. 78 (2005), pp. 1401-1410.
R. J. Koshar et al., "Bis(perfluoroalkylsulfonyl)methanes and Related Disulfones," J. Org. Chem., vol. 38, No. 19 (1973), pp. 3358-3363.
International Search Report (PCT/ISA/210) dated Dec. 24, 2013 with English-language translation (Four (4) pages).

* cited by examiner

*Primary Examiner* — Michael M Bernshteyn
(74) *Attorney, Agent, or Firm* — Crowell & Moring LLP

(57) ABSTRACT

A method for producing compounds containing a bis(perfluoroalkylsulfonyl)methyl group or salts thereof, wherein the compounds have high acidity and hydrophobicity and are useful as raw material compounds for a resin.

11 Claims, No Drawings

METHOD FOR PRODUCING COMPOUND CONTAINING BIS (PERFLUOROALKYLSULFONYL) METHYL GROUP AND SALT THEREOF, AND SOLID ELECTROLYTE MEMBRANE PRODUCED USING SAME

TECHNICAL FIELD

The present invention relates to a method for producing a compound having a bis(perfluoroalkanesulfonyl)methyl group —$CH(SO_2R_f)_2$ where $R_f$ represents a perfluoroalkyl group) and a salt thereof, and to a solid electrolyte membrane produced using the same.

BACKGROUND OF THE INVENTION

A perfluoroalkanesulfonyl group (—$SO_2R_f$) is known to be one of the most strongly electron-withdrawing groups. A bis(perfluoroalkanesulfonyl)methyl group (—$CH(SO_2R_f)_2$) containing two perfluoroalkanesulfonyl groups, in which perfluoroalkanesulfonyl moieties have a strong electron-withdrawing property, tends to release H and therefore exhibits high acidity.

For example, bis(trifluoromethanesulfonyl)methane ($CH_2$($SO_2CF_3)_2$) and phenylbis(trifluoromethanesulfonyl)methane ($PhCH(SO_2CF_3)_2$), either of which contains bis(trifluoromethanesulfonyl) group (—$CH(SO_2CF_3)_2$), are known as strong acids.

In Patent Publications 1 and 2, there is disclosed the introduction of a bis(perfluoroalkanesulfonyl)methyl group to an aromatic compound for the purpose of acquiring an acid catalyst.

In Patent Publication 1, a phenol-based compound containing bis(trifluoromethanesulfonyl)ethyl group is disclosed as a nontoxic acid catalyst that can reduce wastes in the synthesis without subjecting a reactor to corrosion. In order to obtain an aromatic compound containing bis(trifluoromethanesulfonyl)ethyl group, 1,1,3,3-tetrakis(trifluoromethanesulfonyl)propane (($CF_3SO_2)_2CHCH_2CH(SO_2CF_3)_2$) is used and bis(trifluoromethanesulfonyl)ethyl group is introduced into an aromatic phenol derivative or aromatic amine derivative. This reaction utilizes bis(trifluoromethanesulfonyl)ethylene (($CF_3SO_2)_2CHCH_2$) which is generated from 1,1,3,3-tetrakis(trifluoromethanesulfonyl)propane in the reaction system and has high activity, thereby enabling a compound containing bis(trifluoromethanesulfonyl)methyl group to be produced under moderate conditions, from a wide variety of substrates, with high yield.

However, 1,1,3,3-tetrakis(trifluoromethanesulfonyl)propane requires two equivalents of bis(trifluoromethanesulfonyl)methane, and it is necessary to synthesize this compound separately. Moreover, there has been a problem in view of efficiency that, when bis(trifluoromethanesulfonyl)ethylene generates, an equal amount of bis(trifluoromethanesulfonyl)methane is formed as a by-product.

In Patent Publication 2, there is disclosed a polymer support type arylbis(perfluoroalkylsulfonyl)methane represented by the general formula ($RCH(SO_2R_f)(SO_2R_f')$) (where R represents a substituted or unsubstituted aryl group and $R_f$ and $R_f'$ mutually independently represent a perfluoroalkyl group). The polymer support type arylbis(perfluoroalkylsulfonyl)methane can improve the efficiency of a reaction proceeding in the presence of a Broensted acid or a Lewis acid catalyst, for example, facilitates the benzoylation of an alcohol, and can easily be recovered or recycled. Furthermore, Patent Publication 2 mentions that the polymer support type arylbis(perfluoroalkylsulfonyl)methane is usable as a solid catalyst excellent from the viewpoints of toxicity, environments and the like.

In order to obtain the polymer support type arylbis (perfluoroalkylsulfonyl)methane, however, the raw material is limited to a high active aryl halide and requires an excessively large amount of an activating reagent such as a trifluoromethane sulfinate and an easily hydrolizable trifluoromethanesulfonic anhydride and requires to go through a multistage synthetic route under a low temperature and strongly basic condition, which has brought about a problem of complicated synthesis operations.

The introduction of a bis(perfluoroalkanesulfonyl)methyl group into an aromatic compound has thus been reported, but the introduction of a bis(perfluoroalkanesulfonyl)methyl group into an aliphatic compound has been mentioned in a few reports, for example, in Non-Patent Publication 1 and Non-Patent Publication 2.

In Non-Patent Publication 1, there is described a method of producing 1,1-bis(trifluoromethanesulfonyl)octane where octanol ($C_8H_{17}OH$), trifluoromethanesulfinyl chloride ($CF_3SOCl$) and trifluoromethanesulfonic anhydride (($CF_3SO_2)_2O$) are used as raw materials. However, this method causes a multistage reaction requiring much expense in time and effort to be controlled, which reaction is developed in use of an activating reagent not ordinary, and therefore confronts a problem that 1,1-bis(trifluoromethanesulfonyl)octane is not obtained with high yield.

Additionally, Non-Patent Publication 2 discusses a method of introducing a bis(trifluoromethanesulfonyl)methyl group into an aliphatic epoxide compound, in which a Grignard reagent prepared from bis(trifluoromethanesulfonyl)methane and methylmagnesium chloride is reacted with epoxide to prolong the alkyl side chain. However, epoxide is not ordinary and highly decomposable to be used as a raw material, and dehydration conditions adopted at the time of using the Grignard reagent are restricted, and therefore this method is difficult to say a practical one.

Thus, a compound having a bis(perfluoroalkanesulfonyl) methyl group exhibits a high acidity and a hydrophobicity and therefore usable as an acid catalyst and the like. However, a production of a compound having a bis(perfluoroalkanesulfonyl)methyl group bears some problems in that: the synthesis of a raw material is not easy; it requires a multistage stage; and a compound (a reagent) to be reacted with the raw material is unstable and therefore has to be used in an excessively large amount, for example.

Moreover, in U.S. Patent Publications 3 to 5, there is disclosed a method for producing a bis(trifluoromethanesulfonyl)ethylene derivative by a condensation reaction between bis(trifluoromethanesulfonyl)methane and an aldehyde derivative. The raw material is an aromatic aldehyde, a conjugated aldehyde, acetaldehyde or paraformaldehyde, from which the following bis(trifluoroalkanesulfonyl)ethylene compounds are synthesized.

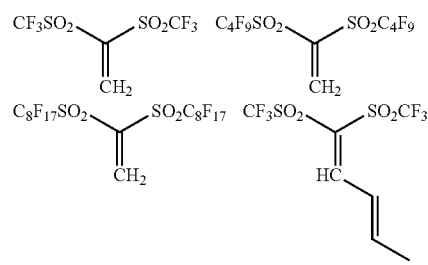

-continued

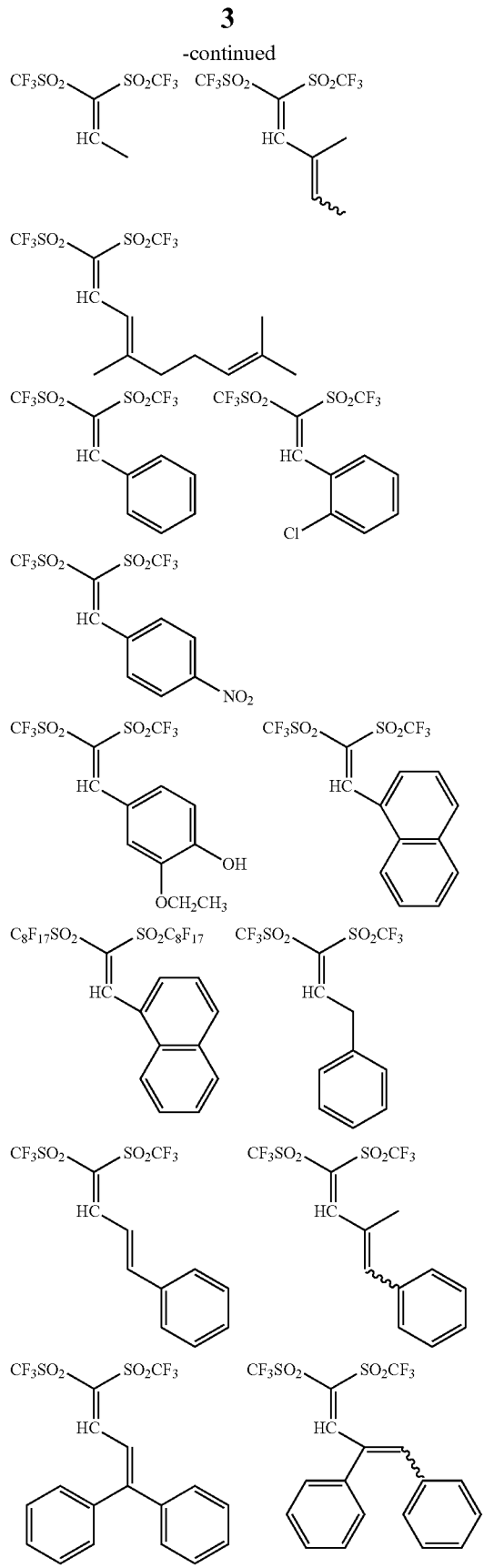

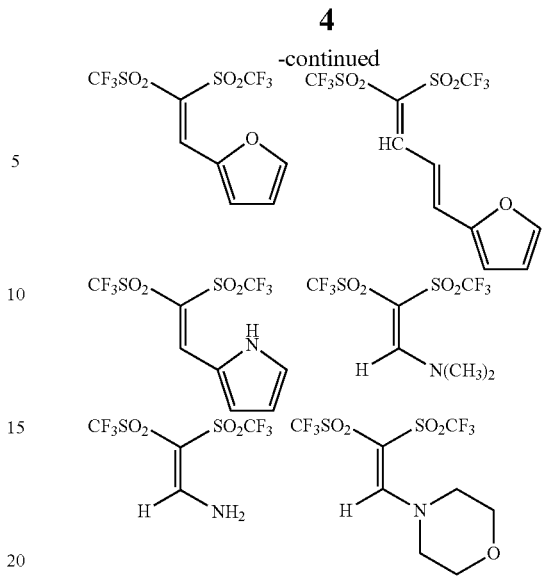

A resin film containing a bis(perfluoroalkanesulfonyl) methyl group (—CH(SO$_2$R$_f$)$_2$) is known to be usable as a solid electrolyte membrane for a polymer electrolyte fuel cell (hereinafter, sometimes referred to as PEFC).

More specifically, a polymer electrolyte fuel cell uses an ion exchange resin membrane (a solid electrolyte membrane) as an electrolyte. Among polymer electrolyte fuel cells, a direct methanol fuel cell (hereinafter, sometimes referred to as DMFC) uses methanol as fuel instead of hydrogen, in which methanol is directly reacted at electrodes to generate electricity. On the contrary to other fuel cells where electrons are released from hydrogen by the action of catalyst on the side of anode (or the side of fuel electrode) thereby separating hydrogen into hydrogen ions (protons) and electrons, in a direct methanol fuel cell methanol is directly reacted with water by the action of catalyst on the anode side to be converted into protons, electrons and carbon dioxide.

As one of objects of the direct methanol fuel cell, it is possible to cite a crossover phenomenon in which a part of methanol permeates through a solid electrolyte from an anode side (a fuel electrode) toward a cathode side (an air electrode). With this phenomenon, fuel is lost and additionally oxygen is consumed by methanol on the air electrode side so as to cause power decline. Hence a development of a solid electrolyte membrane not causing such a methanol permeation is the most important object for sophisticating the performance of a direct methanol fuel cell. In usual cases a resin having a sulfonic acid group is used in a solid electrolyte membrane; however, this membrane holds water firmly by the sulfonic acid group having a strong hydrophilicity, so that the dispersion of methanol is accelerated to enhance methanol permeation.

Patent Publication 6, discloses a solid electrolyte membrane into which a bis(perfluoroalkanesulfonyl)methyl group is introduced, as a solid electrolyte membrane having both a high proton conductivity and a low methanol permeability for suppressing a crossover phenomenon of methanol. By introducing a polyether structure that can be coordinated with water by van der Waals force into a repeating unit containing a hydrophobic and strongly acidic bis(perfluoroalkanesulfonyl)methyl group as an acidic group, it becomes possible to exhibit a high proton conductivity and a low methanol permeation.

REFERENCES ABOUT PRIOR ART

Patent Documents

Patent Publication 1: Japanese Patent Application Publication No. 2012-126688
Patent Publication 2: Japanese Patent Application Publication No. 2002-338539
Patent Publication 3: U.S. Pat. No. 3,932,526
Patent Publication 4: U.S. Pat. No. 3,962,346
Patent Publication 5: U.S. Pat. No. 4,053,519
Patent Publication 6: Japanese Patent Application Publication No. 2011-192640

Non-Patent Documents

Non-Patent Publication 1: H. Yamamoto and K. Ishihara et al., Bull. Chem. Soc. Jap., 78, 1401-1410 (2005)
Non-Patent Publication 2: R. J. Koshar and R. A. Mitsch, J. Org. Chem., 38, 3358-3363 (1973)

SUMMARY OF THE INVENTION

Problems to be Solved by the Invention

Conventional techniques for synthesizing a compound having a bis(perfluoroalkanesulfonyl)methyl group has involved some problems in that: the synthesis of a raw material compound is not easy; the reaction must be multi-stage one; and a compound to be reacted with the raw material (i.e. a reaction reagent) must be used in an excessively large amount because it is so unstable.

An object of the present invention is to provide a method for producing a compound having a bis(perfluoroalkanesulfonyl)methyl group by a simple synthesis reaction.

A further object of the present invention is to provide a solid electrolyte membrane containing a bis(perfluoroalkanesulfonyl)methyl group, the membrane being usable for a polymer electrolyte fuel cell and particularly for a direct methanol fuel cell and having both high proton conductivity and a hydrophobicity to suppress a crossover phenomenon of methanol.

Means for Solving the Problems

As a result of having made studies eagerly, the present inventors attained a method for producing a compound having a bis(perfluoroalkanesulfonyl)methyl group by a simple synthesis reaction with good yield, and attained a novel compound having a bis(perfluoroalkanesulfonyl)methyl group.

A novel norbornene compound having a bis(perfluoroalkanesulfonyl)methyl group can be brought into a solid electrolyte membrane having a norbornene structure.

The present invention involves Inventions 1 to 11.

[Invention 1]

A method for producing a compound represented by the general formula (5), comprising: initiating dehydration condensation between a compound represented by the general formula (1) and an aldehyde compound represented by the general formula (2) or an acetal compound represented by the general formula (3); and then causing reduction with a hydrosilane compound represented by the general formula (4).

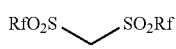
(1)

(In the formula, Rf represents a perfluoroalkyl group having 1 to 12 carbon atoms.)

A—Y—CHO (2)

(In the formula, A represents a monovalent organic group. Y represents a single bond or a $C_1$-$C_4$ linear, $C_3$-$C_4$ branched or $C_3$-$C_4$ cyclic alkylene group wherein each of some or all of hydrogen atoms may be substituted with a fluorine atom, a chlorine atom, a bromine atom or an iodine atom and an ether bond or an ester bond may be contained.)

(3)

(In the formula, $R^1$ and $R^2$ mutually independently represent a $C_1$-$C_{12}$ linear, $C_3$-$C_{12}$ branched or $C_6$-$C_{12}$ cyclic alkyl group. A represents a monovalent organic group. Y represents a single bond or a $C_1$-$C_4$ linear, $C_3$-$C_4$ branched or $C_3$-$C_4$ cyclic alkylene group wherein each of some or all of hydrogen atoms may be substituted with a fluorine atom, a chlorine atom, a bromine atom or an iodine atom and an ether bond or an ester bond may be contained.)

(4)

(In the formula, $R^3$ to $R^5$ mutually independently represent a hydrogen atom or a $C_1$-$C_8$ linear, $C_3$-$C_8$ branched or $C_6$-$C_8$ cyclic alkyl group or a $C_6$-$C_8$ aryl group, in which alkyl group or aryl group each of some or all of hydrogen atoms may be substituted with a fluorine atom, a chlorine atom, a bromine atom or an iodine atom and an ether bond or an ester bond may be contained.)

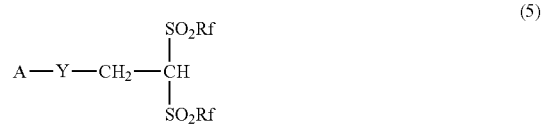
(5)

(In the formula, Rf represents a perfluoroalkyl group having 1 to 12 carbon atoms. A represents a monovalent organic group. Y represents a single bond or a $C_1$-$C_4$ linear, $C_3$-$C_4$ branched or $C_3$-$C_4$ cyclic alkylene group wherein each of some or all of hydrogen atoms may be substituted with a fluorine atom, a chlorine atom, a bromine atom or an iodine atom and an ether bond or an ester bond may be contained.)

[Invention 2]

A production method as discussed in Invention 1, wherein the organic group A is a monovalent organic group represented by the general formula (6), the general formula (7), the general formula (8) or the general formula (9).

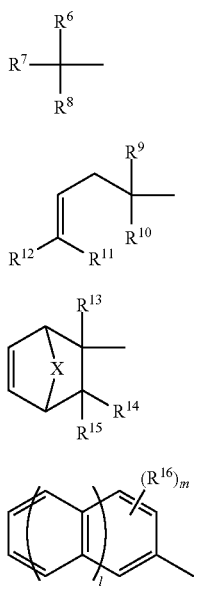

(6)
(7)
(8)
(9)

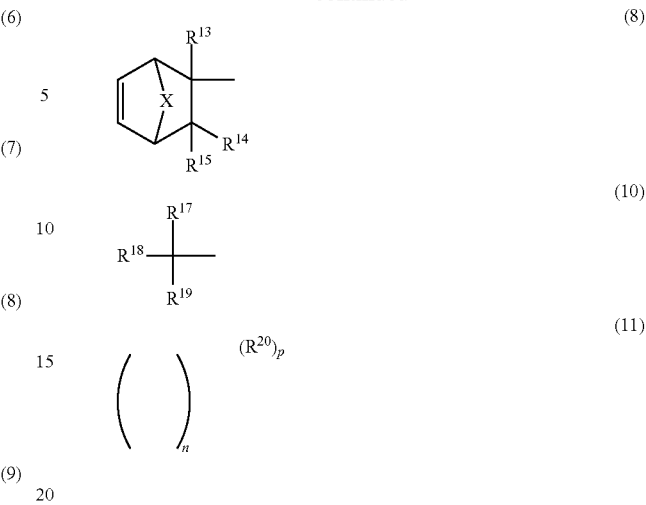

(In the formulas (6) to (8), $R^6$ to $R^{15}$ mutually independently represent a hydrogen atom or a $C_1$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom and an ether bond or an ester bond may be contained. Furthermore, $R^6$ to $R^8$ may be bonded to form a cyclic structure. In the formula (8), X represents $CH_2$, $C(CH_3)_2$ or an oxygen atom. In the formula (9), $R^{16}$ mutually independently represents a hydrogen atom, a fluorine atom, a chlorine atom, a bromine atom, an iodine atom, a nitro group, a sulfonic acid group, a cyano group, a $C_1$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom and an ether bond, an ester bond or a sulfonyl group may be contained. l is an integer between 0 and 2 and m is an integer between 0 and 5.)

[Invention 3]

A compound represented by the general formula (5).

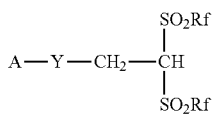

(5)

(In the formula, A represents a monovalent organic group represented by the general formula (7), the general formula (8), the general formula (10) or the general formula (11).

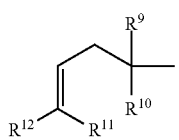

(7)

(In the formulas (7) and (8), $R^9$ to $R^{15}$ mutually independently represent a hydrogen atom or a $C_1$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom and an ether bond or an ester bond may be contained. In the formula (8), X represents $CH_2$, $C(CH_3)_2$ or an oxygen atom. In the formula (10), $R^{17}$ represents a hydrogen atom, a $C_1$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom. $R^{18}$ and $R^{19}$ mutually independently represent a $C_1$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom. Additionally, $R^{17}$ to $R^{19}$ may be bonded to form a cyclic structure. In the formula (11), $R^{20}$ mutually independently represents a fluorine atom, a chlorine atom, a bromine atom, an iodine atom, a nitro group, a sulfonic acid group, a cyano group, a $C_2$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom and each of some of carbon atoms may be substituted with a sulfur atom and a carbonyl group or a sulfonyl group may be contained. n is an integer between 0 and 2 and p is an integer between 1 and 5.) Rf represents a perfluoroalkyl group having 1 to 12 carbon atoms. Y represents a single bond or a $C_1$-$C_4$ linear, $C_3$-$C_4$ branched or $C_3$-$C_4$ cyclic alkylene group wherein each of some or all of hydrogen atoms may be substituted with a fluorine atom, a chlorine atom, a bromine atom or an iodine atom and an ether bond or an ester bond may be contained.)

[Invention 4]

A method for producing a salt represented by the general formula (12), comprising: causing neutralization reaction of a compound represented by the general formula (5), with an alkali metal salt.

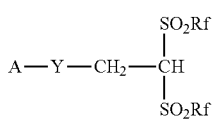
(5)

(In the formula, Rf represents a perfluoroalkyl group having 1 to 12 carbon atoms. A represents a monovalent organic group. Y represents a single bond or a $C_1$-$C_4$ linear, $C_3$-$C_4$ branched or $C_3$-$C_4$ cyclic alkylene group wherein each of some or all of hydrogen atoms may be substituted with a fluorine atom, a chlorine atom, a bromine atom or an iodine atom and an ether bond or an ester bond may be contained.)

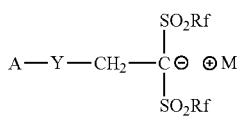
(12)

(In the formula, Rf represents a perfluoroalkyl group having 1 to 12 carbon atoms. A represents a monovalent organic group. Y represents a single bond or a $C_1$-$C_4$ linear, $C_3$-$C_4$ branched or $C_3$-$C_4$ cyclic alkylene group wherein each of some or all of hydrogen atoms may be substituted with a fluorine atom, a chlorine atom, a bromine atom or an iodine atom and an ether bond or an ester bond may be contained. M represents an alkali metal ion or an ammonium ion.)

[Invention 5]
A method for producing a salt, as discussed in Invention 4, wherein the organic group A is a monovalent organic group represented by the general formula (6), the general formula (7), the general formula (8) or the general formula (9).

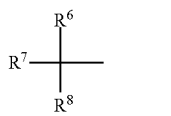
(6)

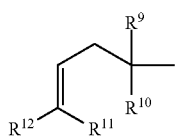
(7)

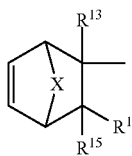
(8)

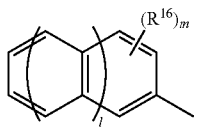
(9)

(In the formulas (6) to (8), $R^6$ to $R^{15}$ mutually independently represent a hydrogen atom or a $C_1$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom and an ether bond or an ester bond may be contained. Furthermore, $R^6$ to $R^8$ may be bonded to form a cyclic structure. In the formula (8), X represents $CH_2$, $C(CH_3)_2$ or an oxygen atom. In the formula (9), $R^{16}$ mutually independently represents a hydrogen atom, a fluorine atom, a chlorine atom, a bromine atom, an iodine atom, a nitro group, a sulfonic acid group, a cyano group, a $C_1$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom and an ether bond, an ester bond or a sulfonyl group may be contained. l is an integer between 0 and 2 and m is an integer between 0 and 5.)

[Invention 6]
A salt represented by the general formula (12).

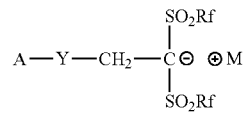
(12)

(A represents a monovalent organic group represented by the general formula (7), the general formula (8), the general formula (10) or the general formula (11).

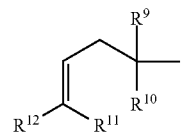
(7)

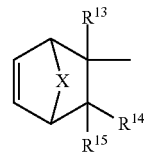
(8)

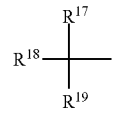
(10)

(11)

(In the formulas (7) and (8), $R^9$ to $R^{15}$ mutually independently represent a hydrogen atom or a $C_1$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom and an ether bond or an ester bond may be contained. In the formula (8), X represents $CH_2$, $C(CH_3)_2$ or an oxygen atom. In the formula (10), $R^{17}$ represents a hydrogen atom, a $C_1$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom. $R^{18}$ and $R^{19}$ mutually independently represent a $C_1$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom. Additionally, $R^{17}$ to $R^{19}$ may be bonded to form a cyclic structure. In the formula (11), $R^{20}$ mutually independently represents a fluorine atom, a chlorine atom, a bromine atom, an iodine atom, a nitro group, a sulfonic acid group, a cyano group, a $C_2$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom and each of some of carbon atoms may be substituted with a sulfur atom and a carbonyl group or a sulfonyl group may be contained. l is an integer between 0 and 2 and m is an integer between 1 and 5.) Rf represents a perfluoroalkyl group having 1 to 12 carbon atoms. Y represents a single bond or a $C_1$-$C_4$ linear, $C_3$-$C_4$ branched or $C_3$-$C_4$ cyclic alkylene group wherein each of some or all of hydrogen atoms may be substituted with a fluorine atom, a chlorine atom, a bromine atom or an iodine atom and an ether bond or an ester bond may be contained. M represents an alkali metal ion or an ammonium ion.)

[Invention 7]

A polymer comprising a repeating unit having a bis (perfluoroalkanesulfonyl)methyl group and selected from the group consisting of the general formula (8-A), the general formula (8-B) and the general formula (8-C).

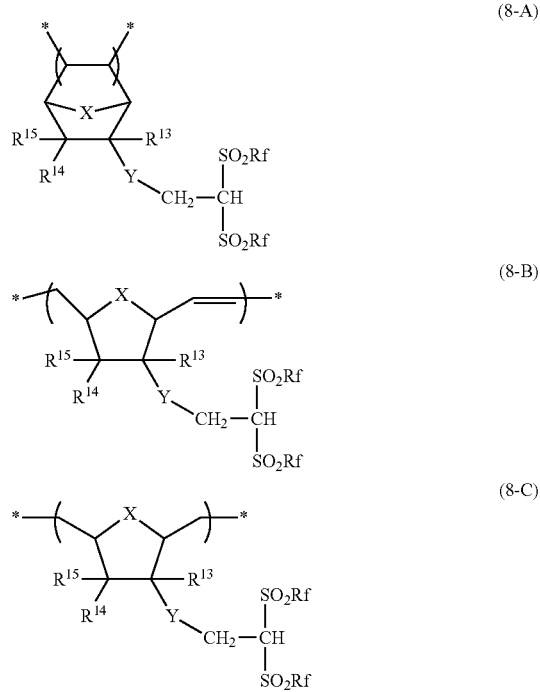

(8-A)
(8-B)
(8-C)

(In the formula (8-A) to the formula (8-C), Rf represents a perfluoroalkyl group having 1 to 12 carbon atoms. $R^{13}$ to $R^{15}$ mutually independently represent a hydrogen atom or a $C_1$-$C_{12}$ linear, $C_3$-$C_{12}$ branched or $C_3$-$C_{12}$ cyclic alkyl group or a $C_6$-$C_{12}$ aryl group, in which alkyl group or aryl group each of some or all of hydrogen atoms may be substituted with a fluorine atom, a chlorine atom, a bromine atom or an iodine atom and an ether bond or an ester bond may be contained. X represents $CH_2$, $C(CH_3)_2$ or an oxygen atom. Y represents a single bond or a $C_1$-$C_4$ linear, $C_3$-$C_4$ branched or $C_3$-$C_4$ cyclic alkylene group wherein each of some or all of hydrogen atoms may be substituted with a fluorine atom, a chlorine atom, a bromine atom or an iodine atom and an ether bond or an ester bond may be contained. In the formula, an asterisk "*" represents a bonding hand.)

[Invention 8]

A solid electrolyte membrane comprising a polymer as discussed in Invention 7.

[Invention 9]

A membrane electrode assembly for fuel cells, comprising a solid electrolyte membrane as discussed in Invention 8.

[Invention 10]

A polymer electrolyte fuel cell comprising a solid electrolyte membrane as discussed in Invention 8.

[Invention 11]

A direct methanol fuel cell comprising a solid electrolyte membrane as discussed in Invention 8.

Effects of the Invention

In the production method according to the present invention, a compound having a bis(perfluoroalkanesulfonyl) methyl group and a salt thereof were obtained through a simple synthesis reaction with good yield.

Moreover, the compound obtained by the method for producing a compound having a bis(perfluoroalkanesulfonyl)methyl group according to the present invention was polymerized, and the thus produced polymer was used, thereby providing a solid electrolyte membrane usable for a polymer electrolyte fuel cell and particularly for a direct methanol fuel cell which membrane has both high proton conductivity and a hydrophobicity to suppress a crossover phenomenon of methanol.

MODE(S) FOR CARRYING OUT THE INVENTION

Hereinafter, the present invention will be discussed with reference to some embodiments; however, the present invention is not limited to the following embodiments and it may suitably be embodied within a range not to affect the scope of the present invention on the basis of the understanding common among persons skilled in the art.

The present invention relates to a method for producing a compound having a bis(perfluoroalkanesulfonyl)methyl group a salt thereof and to a solid electrolyte membrane produced using the same, which will be described step by step.

1. Method for Producing Compound Having Bis(perfluoroalkanesulfonyl)methyl Group A method for producing a compound having a bis(perfluoroalkanesulfonyl)methyl group, according to the present invention involves the above-mentioned Inventions 1 and 2.

Hereinafter, there will be discussed a reaction path of the reaction developed in the method for producing a compound having a bis(perfluoroalkanesulfonyl)methyl group and represented by the general formula (5).

1-1. Reaction Path

The present invention is a method for producing a compound (5) having a bis(perfluoroalkanesulfonyl)methyl group and represented by the general formula (5) which method comprises: initiating dehydration condensation reaction between a compound represented by the general formula (1) (i.d. bis(perfluoroalkanesulfonyl)methane) and an aldehyde compound (2) represented by the general formula (2) or an acetal compound (3) represented by the general formula (3); and then causing reduction reaction with a hydrosilane compound (4) represented by the general formula (4). This is shown in the following reaction path.

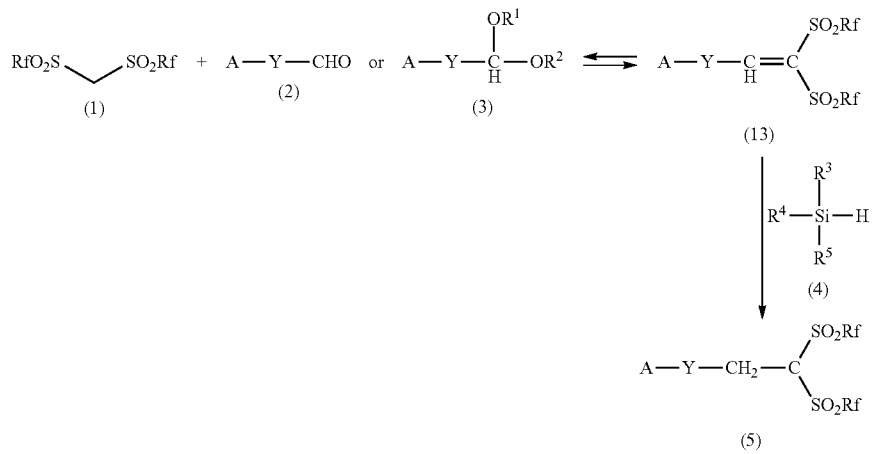

A bis(perfluoroalkanesulfonyl)ethylene compound (13) represented by the general formula (13) is obtained by causing dehydration condensation reaction between a bis(perfluoroalkanesulfonyl)methane compound (1) represented by the general formula (1) and an aldehyde compound (2) represented by the general formula (2) or an acetal compound (3) represented by the general formula (3). However, a bis(perfluoroalkanesulfonyl)ethylene compound (13) represented by the general formula (13) is an unstable compound, which tends to hydrolyze and inhibits the reaction and difficult to isolate from the reaction system.

Patent Publications 3 to 5 describe isolatable types of a bis(perfluoroalkanesulfonyl)ethylene compound (13) as mentioned above, but only describe some kinds of compound having undergone stabilization by any steric factor, conjugation with an aromatic ring or unsaturated bond or the like.

In the method of the present invention for producing a compound represented by the general formula (5), i.e. in the method for producing a compound (5) having a bis(perfluoroalkanesulfonyl)methyl group, an unstable bis(perfluoroalkanesulfonyl)ethylene compound (13) represented by the general formula (13) is reduced without being isolated from the reaction system, by adding a hydrosilane compound (4) represented by the general formula (4) into the reaction system under moderate conditions. With this, it becomes possible to synthesize a stable bis(perfluoroalkanesulfonyl)methyl compound (5) represented by the general formula (5) and additionally the operation is simple.

Incidentally, "$R_f$" included in compounds (1), (5) and (13) is a perfluoroalkyl group having 1 to 12 carbon atoms. Concrete examples of $R_f$ are trifluoromethyl group, pentafluoroethyl group, perfluoropropyl group, perfluorobutyl group, perfluorohexyl group, perfluorooctyl group and perfluorododecyl group. Trifluoromethyl group, perfluorobutyl group and perfluorooctyl group are preferable.

$R^1$ and $R^2$ as shown in a compound (3) mutually independently represent a $C_1$-$C_{12}$ linear, $C_3$-$C_{12}$ branched or $C_6$-$C_{12}$ cyclic alkyl group.

Concrete examples of $R^1$ and $R^2$ are methyl group, ethyl group, n-propyl group, i-propyl group, n-butyl group, t-butyl group, n-pentyl group, i-pentyl group, n-hexyl group, i-hexyl group, n-heptyl group, n-octyl group, i-octyl group, n-nonyl group, n-decyl group, n-dodecyl group, cyclopropyl group, cyclobutyl group, cyclopentyl group, cyclohexyl group, adamantylmethyl group and 2-norbornylmethyl group. Methyl group, ethyl group and i-propyl group are preferable.

$R^3$ to $R^5$ as shown in a compound (4) mutually independently represent a hydrogen atom or a $C_1$-$C_8$ linear, $C_3$-$C_8$ branched or $C_6$-$C_8$ cyclic alkyl group or a $C_6$-$C_8$ aryl group.

Concrete examples of the alkyl group are methyl group, ethyl group, n-propyl group, i-propyl group, n-butyl group, t-butyl group, n-pentyl group, i-pentyl group, n-hexyl group, i-hexyl group, n-heptyl group, n-octyl group, i-octyl group, cyclopropyl group, cyclobutyl group, cyclopentyl group and cyclohexyl group. Concrete examples of aryl group are phenyl group and tolyl group. Methyl group, ethyl group, i-propyl group and phenyl group are preferable.

In the alkyl group or the aryl group, each of some or all of hydrogen atoms may be substituted with a fluorine atom, a chlorine atom, a bromine atom or an iodine atom and an ether bond or an ester bond may be contained.

1-2. Organic Group A

An organic group "A" is an alkyl group, an alkenyl group, an alkynyl group or an aryl group, in which each of some or all of hydrogen atoms may be substituted with a fluorine atom, a chlorine atom, a bromine atom or an iodine atom and an ether bond, an ester bond or a sulfonyl group may be contained.

In a compound (2), a compound (3) and a compound (5), it is preferable that the organic group A is a monovalent organic group represented by the general formula (6), the general formula (7), the general formula (8) or the general formula (9).

-continued

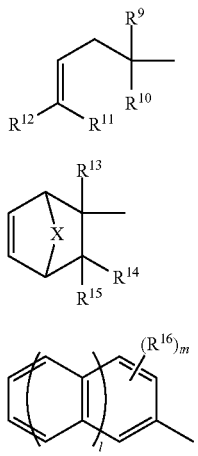

In the formulas (6) to (8), $R^6$ to $R^{15}$ mutually independently represent a hydrogen atom or a $C_1$-$C_{12}$ linear, $C_3$-$C_{12}$ branched or $C_3$-$C_{12}$ cyclic alkyl group or a $C_6$-$C_{12}$ aryl group.

Concrete examples of the alkyl group are methyl group, ethyl group, n-propyl group, i-propyl group, n-butyl group, t-butyl group, n-pentyl group, i-pentyl group, n-hexyl group, i-hexyl group, n-heptyl group, n-octyl group, i-octyl group, n-nonyl group, n-decyl group, n-dodecyl group, cyclopropyl group, cyclobutyl group, cyclopentyl group, cyclohexyl group, adamantylmethyl group and 2-norbornylmethyl group. Concrete examples of the aryl group are phenyl group, 1-naphthyl group, 2-naphthyl group, 1-anthryl group and 1-phenanthryl group. Methyl group, ethyl group, 2-norbornylmethyl group and phenyl group are preferable.

In the alkyl group or the aryl group, each of some or all of hydrogen atoms may be substituted with a fluorine atom, a chlorine atom, a bromine atom or an iodine atom and an ether bond or an ester bond may be contained.

In organic group (8), X preferably represents $CH_2$, $C(CH_3)_2$ or an oxygen atom. In organic group (8), these groups are general. Heteroatom other than oxygen atom can possibly inhibit the above-mentioned reaction.

In organic group (9), $R^{16}$ can mutually independently be exemplified by a hydrogen atom, a fluorine atom, a chlorine atom, a bromine atom, an iodine atom, a nitro group, a sulfonic acid group, a cyano group, a $C_1$-$C_{12}$ linear, $C_3$-$C_{12}$ branched or $C_3$-$C_{12}$ cyclic alkyl group or a $C_6$-$C_{12}$ aryl group.

Concrete examples of the alkyl group are methyl group, ethyl group, n-propyl group, i-propyl group, n-butyl group, t-butyl group, n-pentyl group, i-pentyl group, n-hexyl group, i-hexyl group, n-heptyl group, n-octyl group, i-octyl group, n-nonyl group, n-decyl group, n-dodecyl group, cyclopropyl group, cyclobutyl group, cyclopentyl group, cyclohexyl group, adamantylmethyl group and 2-norbornylmethyl group. Concrete examples of the aryl group are phenyl group, 1-naphthyl group, 2-naphthyl group, 1-anthryl group and 1-phenanthryl group. Methyl group, ethyl group, n-propyl group and phenyl group are preferable.

In the alkyl group or the aryl group, each of some or all of hydrogen atoms may be substituted with a fluorine atom, a chlorine atom, a bromine atom or an iodine atom and an ether bond, an ester bond or a sulfonyl group may be contained.

In organic group (9), l represents any integer between 0 and 2 and m represents any integer between 0 and 5. If the number of $R^{16}$ is two or more, it is not inquired whether l and m are identical or different.

1-3. Compound in Reaction Path

In a compound (2), a compound (3) and a compound (5) in the above-mentioned reaction path, Y represents a single bond or a $C_1$-$C_4$ linear, $C_3$-$C_4$ branched or $C_3$-$C_4$ cyclic alkylene group.

Concrete examples of the alkylene group are methylene group, ethylene group, n-propylene group, i-propylene group, n-butylene group, cyclopropylene group and cyclobutylene group. Methylene group and ethylene group are preferable.

Additionally, in the alkylene group, each of some or all of hydrogen atoms may be substituted with a fluorine atom, a chlorine atom, a bromine atom or an iodine atom and an ether bond or an ester bond may be contained.

A compound (2) can be exemplified by the following compounds:

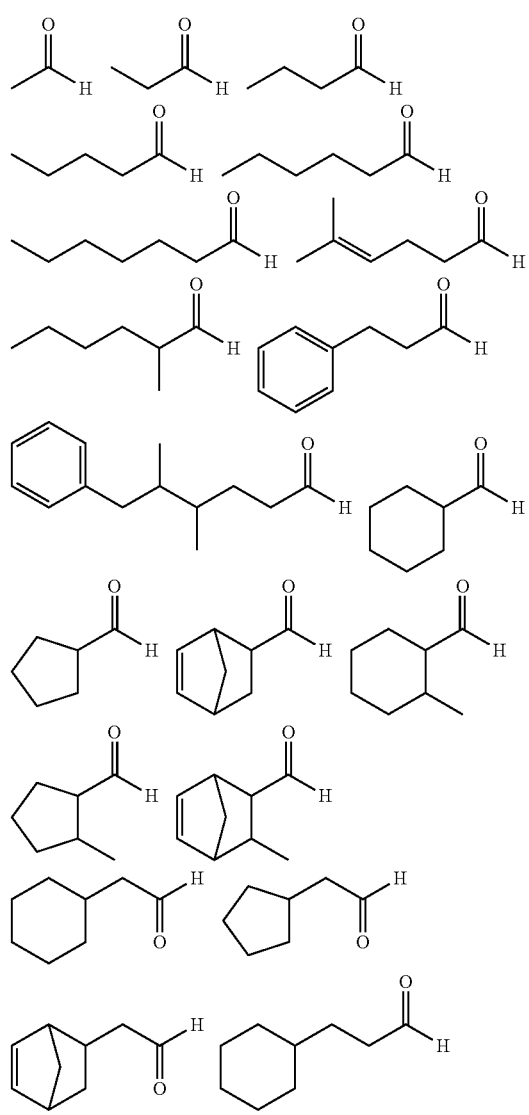

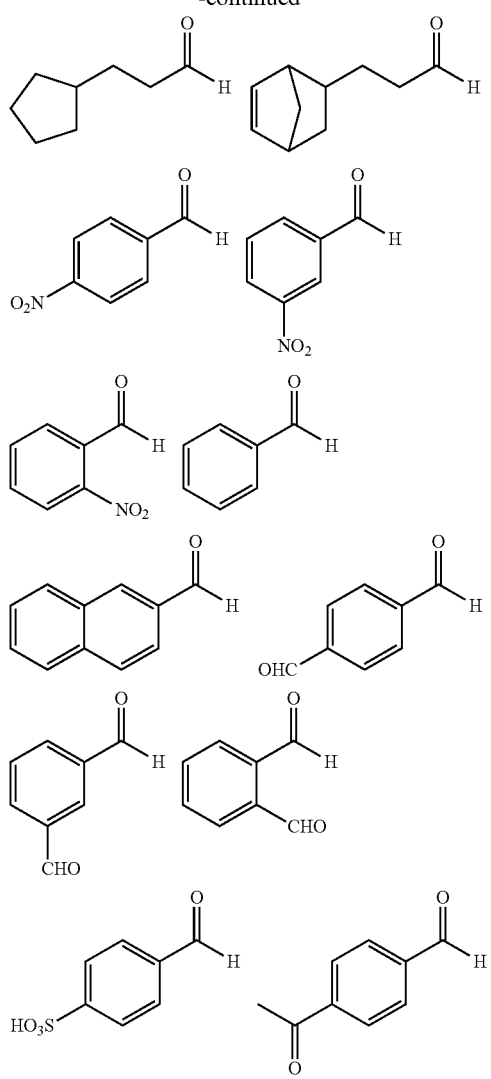
and more preferably by the following compounds.
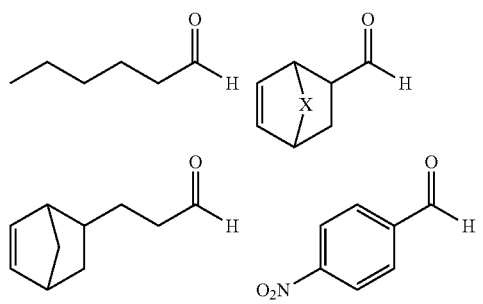
A compound (3) can be exemplified by the following compounds:
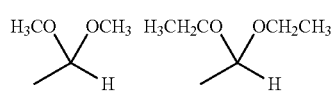
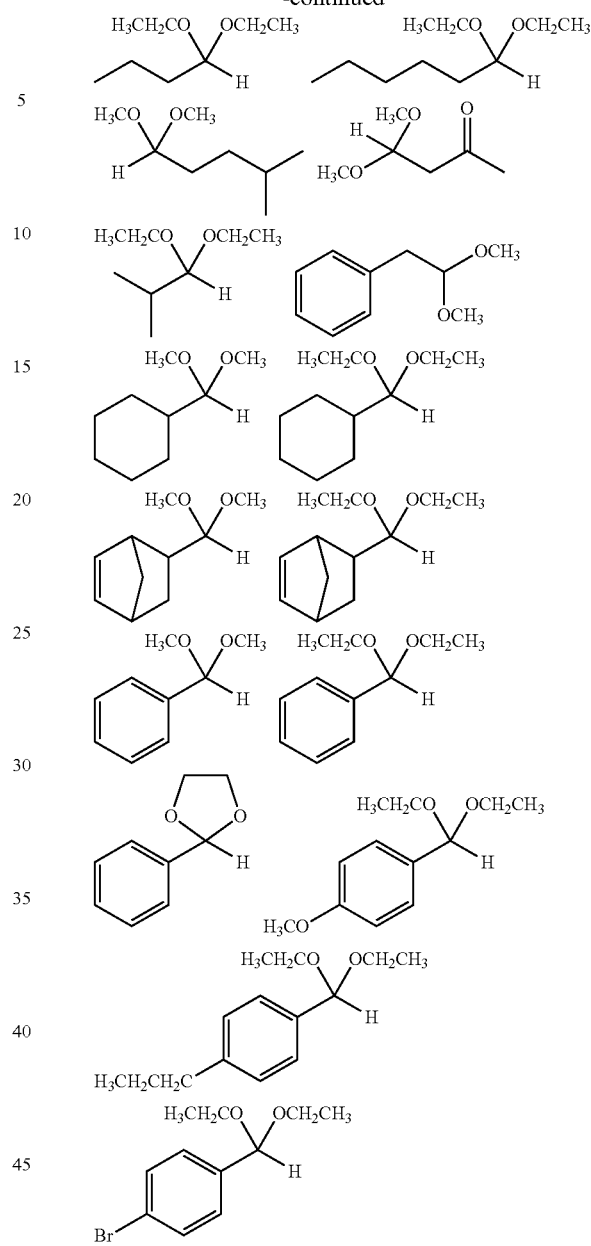
and more preferably by the following compounds.
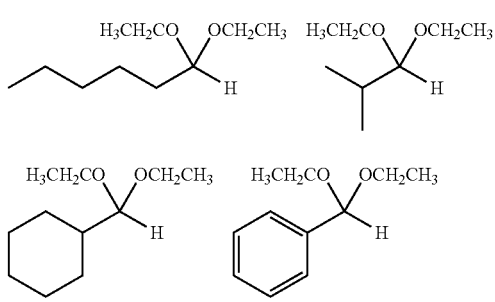

A compound (3) can be exemplified by the following compounds:

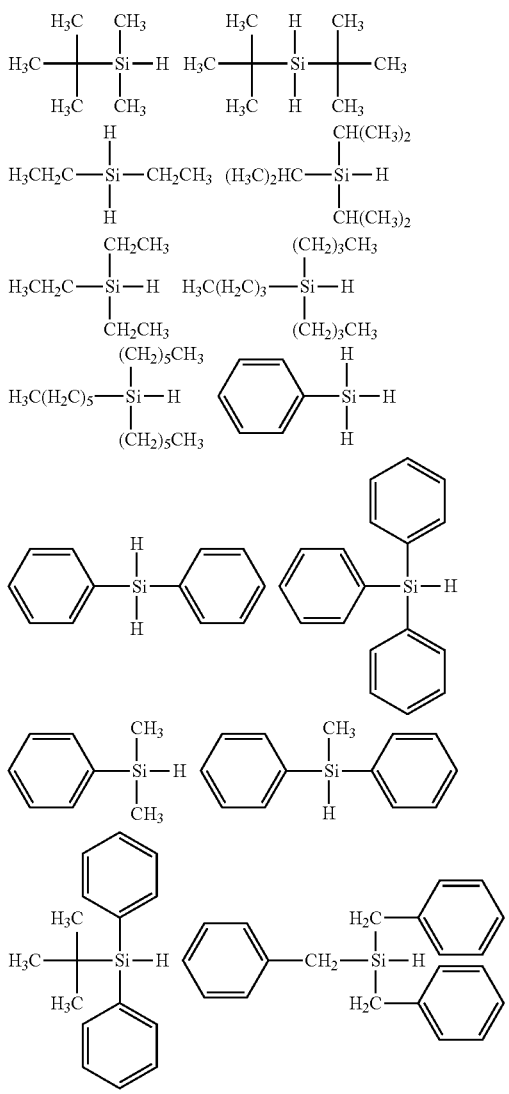

and more preferably by the following compounds.

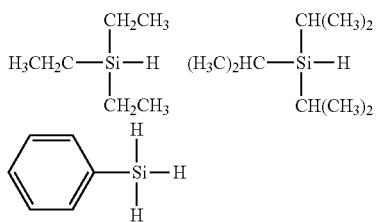

1-4. Production of Compound (5)

In producing a compound (5), which is a target product, a synthesis reaction may be performed in the presence of a solvent. The reaction solvent is not particularly limited unless it participates in the reaction and exemplified by: saturated hydrocarbons such as n-pentane, n-hexane, n-heptane and n-octane; aromatic hydrocarbons such as benzene, toluene and xylene; ethers such as diethyl ether, diisopropyl ether, tetrahydrofuran and dioxane; halogenated hydrocarbons such as dichloromethane, 1,2-dichloroethane and chloroform; alcohols such as methanol, ethanol and isopropanol; ketones such as acetone, methyl ethyl ketone; and aprotic polar solvents such as acetonitrile, N,N-dimethylformamide (DMF), dimethyl sulfoxide (DMSO) and hexamethyl phosphoramide (HMPA). It is preferable to use diethyl ether, diisopropyl ether, dichloromethane or toluene, more preferably dichloromethane or toluene.

The reaction temperature is preferably 0 to 120° C., which may suitably be adjusted according to the boiling point of the reaction solvent or according to the progress of the reaction within the above-mentioned temperature range.

As a purification method for a compound (5), it is possible to employ purification methods general in organic synthesis, such as recrystallization, distillation, column chromatography and the like. By these means, a compound (5) can be obtained. Among these methods, distillation method is preferably adopted since a compound (5) is most easily obtained with high purity and high yield. Distillation is preferably adopted in producing a compound (5) on an industrial scale.

Incidentally, at the time of distillation, it may be performed at normal pressure (0.1 MPa) but preferably performed under a reduced pressure. Under a reduced pressure condition, distillation can be carried out at a relatively low temperature. Furthermore, a distillation column formed of glass or stainless steel and a distillation column that has been subjected at inside to lining with tetrafluoroethylene resin, chlorotrifluoroethylene resin, vinylidene fluoride resin, PFA resin or glass are also acceptable. It is also possible to fill the distillation column with a filler.

In producing a compound (5), the synthesis reaction may be performed by using an aldehyde compound (2) and an acetal compound (3) concurrently. However, in order to obtain a compound (5) as a single compound with good yield, and from the viewpoint of easiness of reaction and easiness of purification operations, it is preferable to cause a synthesis reaction of a compound (5) by using either one of an aldehyde compound (2) and an acetal compound (3).

2. Novel Compound Having Bis(perfluoroalkanesulfonyl) methyl Group

A novel compound having a bis(perfluoroalkanesulfonyl) methyl group, according to the present invention is as has been discussed in Invention 3.

In a compound (5), "A" represents a monovalent organic group. Additionally, it is preferable that A is a monovalent organic group represented by the general formula (7), the general formula (8), the general formula (10) or the general formula (11).

(7)

(8)

(10)

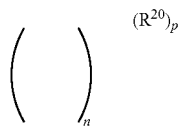

In the formulas (7) and (8), $R^9$ to $R^{15}$ mutually independently represent a hydrogen atom or a $C_1$-$C_{12}$ linear, $C_3$-$C_{12}$ branched or $C_3$-$C_{12}$ cyclic alkyl group or a $C_6$-$C_{12}$ aryl group.

Among $R^9$ to $R^{15}$, concrete examples of the $C_1$-$C_{12}$ linear, $C_3$-$C_{12}$ branched or $C_3$-$C_{12}$ cyclic alkyl group are methyl group, ethyl group, n-propyl group, i-propyl group, n-butyl group, t-butyl group, n-pentyl group, i-pentyl group, n-hexyl group, i-hexyl group, n-heptyl group, n-octyl group, i-octyl group, n-nonyl group, n-decyl group, n-dodecyl group, cyclopropyl group, cyclobutyl group, cyclopentyl group, cyclohexyl group, adamantylmethyl group and 2-norbornyl-methyl group. Concrete examples of the $C_6$-$C_{12}$ aryl group are phenyl group, 1-naphthyl group, 2-naphthyl group, 1-anthryl group and 1-phenanthryl group. Methyl group, ethyl group and phenyl group are preferable.

Furthermore, in the alkyl group or the aryl group, each of some or all of hydrogen atoms may be substituted with a fluorine atom, a chlorine atom, a bromine atom or an iodine atom and an ether bond or an ester bond may be contained.

In the formula (8), X represents $CH_2$, $C(CH_3)_2$ or an oxygen atom.

In the formula (10), $R^{17}$ represents a hydrogen atom, a $C_1$-$C_{12}$ linear, $C_3$-$C_{12}$ branched or $C_3$-$C_{12}$ cyclic alkyl group or a $C_6$-$C_{12}$ aryl group. $R^{18}$ and $R^{19}$ mutually independently represent a $C_1$-$C_{12}$ linear, $C_3$-$C_{12}$ branched or $C_3$-$C_{12}$ cyclic alkyl group or a $C_6$-$C_{12}$ aryl group. $R^{17}$ to $R^{19}$ may be bonded to form a cyclic structure.

Additionally, in the alkyl group or the aryl group, each of some or all of hydrogen atoms may be substituted with a fluorine atom, a chlorine atom, a bromine atom or an iodine atom.

In the formula (11), $R^{20}$ mutually independently represents a fluorine atom, a chlorine atom, a bromine atom, an iodine atom, a nitro group, a sulfonic acid group, a cyano group, a $C_2$-$C_{12}$ linear, $C_3$-$C_{12}$ branched or $C_3$-$C_{12}$ cyclic alkyl group or a $C_6$-$C_{12}$ aryl group.

Concrete examples of the $C_2$-$C_{12}$ linear alkyl group are ethyl group, n-propyl group, n-butyl group, n-pentyl group, n-hexyl group, i-hexyl group, n-heptyl group, n-octyl group, n-nonyl group, n-decyl group and n-dodecyl group. Ethyl group, n-propyl group and n-butyl group are preferable.

A concrete structure of the $C_3$-$C_{12}$ branched or $C_3$-$C_{12}$ cyclic alkyl group or the $C_6$-$C_{12}$ aryl group is identical to $R^9$ to $R^{15}$ of organic groups (7) and (8).

Moreover, in the alkyl group or the aryl group, each of some or all of hydrogen atoms may be substituted with a fluorine atom, a chlorine atom, a bromine atom or an iodine atom and each of some of carbon atoms may be substituted with a sulfur atom and a carbonyl group or a sulfonyl group may be contained.

"n" is any integer between 0 and 2 and "p" is any integer between 1 and 5. If the number of $R^{11}$ is two or more, it is not inquired whether n and p are identical or different.

In the general formula (5), Y represents a single bond or a $C_1$-$C_4$ linear, $C_3$-$C_4$ branched or $C_3$-$C_4$ cyclic alkylene group.

Concrete examples of the $C_1$-$C_4$ linear, $C_3$-$C_4$ branched or $C_3$-$C_4$ cyclic alkylene group are methylene group, ethylene group, n-propylene group, i-propylene group, n-butylene group, cyclopropylene group and cyclobutylene group. Methylene group and ethylene group are preferable.

Additionally, in the alkylene group, each of some or all of hydrogen atoms may be substituted with a fluorine atom, a chlorine atom, a bromine atom or an iodine atom and an ether bond or an ester bond may be contained.

A compound (5) can concretely be exemplified by the following compounds:

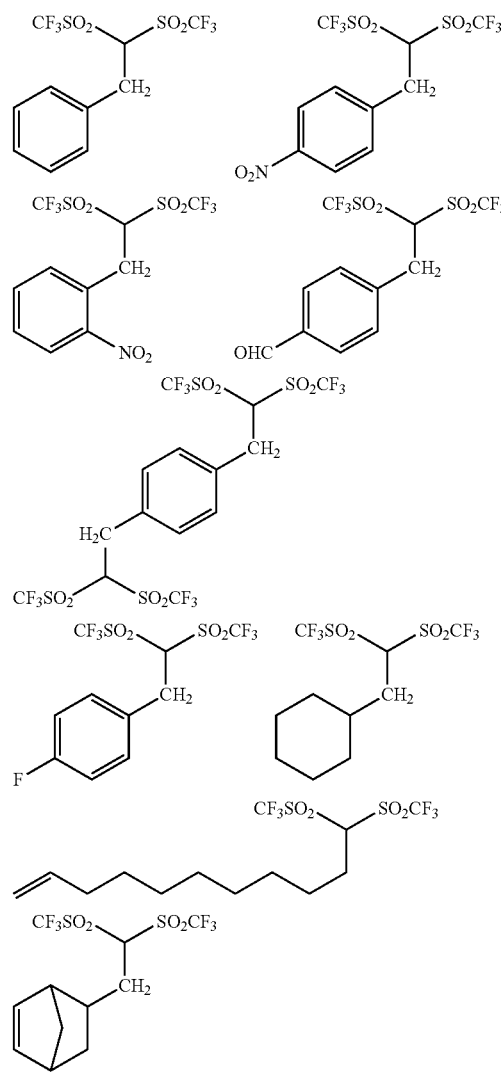

and more preferably by the following compounds.

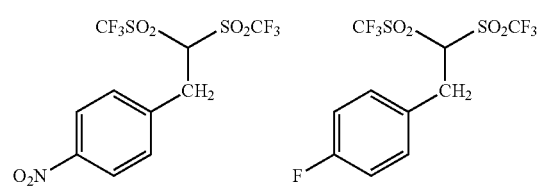

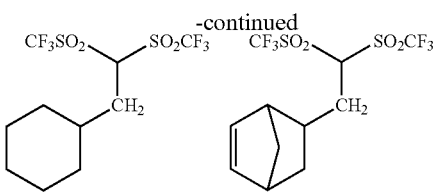

A compound represented by the general formula (5) has a high acidity by virtue of a bis(perfluoroalkanesulfonyl)methyl group regardless of the presence of a polymerizable group, and therefore useful as an acid catalyst. A compound represented by the general formula (5) is soluble in a variety of solvents so as to be usable in various kinds of organic synthesis reactions as an aid catalyst. Furthermore, a compound represented by the general formula (5) has a low nucleophilicity of conjugate base while having acidity; consequently, this compound is difficult to cause decomposition reaction and therefore easily separated from the target compound after reaction.

Among compounds represented by the general formula (5), a compound having a polymerizable group represented by the general formula (7) or the general formula (8) may be polymerized singly or copolymerized with acrylic monomer or the like.

Method for Producing Salt Having Bis(perfluoroalkanesulfonyl)methyl Group

In Inventions 4 and 5, a method for producing a salt having a bis(perfluoroalkanesulfonyl)methyl group is as has been discussed in Inventions 4 and 5.

A salt (12) is obtained by causing neutralization reaction of a compound represented by the general formula (5), with an alkali metal salt or an amine compound.

Neutralization reaction is not particularly limited, so that a publicly known method is applicable. For example, the reaction can be developed by exerting a bis(pefluoroalkanesulfonyl)methyl group on an equivalent amount of an alkali metal salt (e.g. lithium hydroxide, sodium hydroxide, potassium hydroxide, sodium carbonate, potassium carbonate, cesium carbonate and sodium hydrogencarbonate) or an amine compound (e.g. methylamine, ethylamine, dimethylamine, diethylamine, trimethylamine and triethylamine) in water and an organic solvent.

An organic solvent to be used in the above-mentioned method is required only to be one that can dissolve a produced salt therein, and exemplified by: hydrocarbon-based solvents such as benzene and toluene; halogenated hydrocarbon-based solvents such as dichloromethane and chloroform; ketone-based solvents such as methyl ethyl ketone, methyl isobutyl ketone and cyclohexanone, ester-based solvents such as ethyl acetate and butyl acetate; and ether-based solvents such as tetrahydrofuran and 1,4-dioxane. These solvents may be used singly or in combination.

The amount of the organic solvent to be used is not particularly limited, but preferably 20 to 500 parts by mass, more preferably 100 to 300 parts by mass relative to 100 parts by mass of a compound (5) in normal cases. Additionally, neutralization reaction can be performed at a temperature of not lower than 0° C. and not higher than the boiling point of the organic solvent, under atmospheric pressure or an applied pressure. After neutralization reaction, a salt (the target product) is dissolved in water, followed by separating a water layer or removing the organic solvent, thereby obtaining a salt. As a method of removing the organic solvent, the organic solvent may be heated under atmospheric or reduced pressure to the boiling point of the organic solvent or more to be removed.

4. Novel Salt Having Bis(trifluoroalkanesulfonyl)methyl Group

A novel salt having a bis(perfluoroalkanesulfonyl)methyl group, according to the present invention is as has been discussed in the above-mentioned Invention 6.

More specifically, a salt represented by the general formula (12) in Invention 6 is an alkali metal salt or an ammonium compound.

Among $R^9$ to $R^{15}$, concrete examples of the $C_1$-$C_{12}$ linear, $C_3$-$C_{12}$ branched or $C_3$-$C_{12}$ cyclic alkyl group are methyl group, ethyl group, n-propyl group, i-propyl group, n-butyl group, t-butyl group, n-pentyl group, i-pentyl group, n-hexyl group, i-hexyl group, n-heptyl group, n-octyl group, i-octyl group, n-nonyl group, n-decyl group, n-dodecyl group, cyclopropyl group, cyclobutyl group, cyclopentyl group, cyclohexyl group, adamantylmethyl group and 2-norbornylmethyl group. Concrete examples of the $C_6$-$C_{12}$ aryl group are phenyl group, 1-naphthyl group, 2-naphthyl group, 1-anthryl group and 1-phenanthryl group. Methyl group, ethyl group and phenyl group are preferable.

In the alkyl group or the aryl group, each of some or all of hydrogen atoms may be substituted with a fluorine atom, a chlorine atom, a bromine atom or an iodine atom and an ether bond or an ester bond may be contained.

In the formula (8), X represents $CH_2$, $C(CH_3)_2$ or an oxygen atom.

In the formula (10), $R^{17}$ represents a hydrogen atom, a $C_1$-$C_{12}$ linear, $C_3$-$C_{12}$ branched or $C_3$-$C_{12}$ cyclic alkyl group or a $C_6$-$C_{12}$ aryl group. $R^{18}$ and $R^{19}$ mutually independently represent a $C_1$-$C_{12}$ linear, $C_3$-$C_{12}$ branched or $C_3$-$C_{12}$ cyclic alkyl group or a $C_6$-$C_{12}$ aryl group. $R^{17}$ to $R^{19}$ may be bonded to form a cyclic structure.

A concrete structure of the alkyl group or the aryl group is identical to $R^9$ to $R^{15}$ of organic groups (7) and (8).

In the alkyl group or the aryl group, each of some or all of hydrogen atoms may be substituted with a fluorine atom, a chlorine atom, a bromine atom or an iodine atom.

In the formula (11), $R^{20}$ mutually independently represents a fluorine atom, a chlorine atom, a bromine atom, an iodine atom, a nitro group, a sulfonic acid group, a cyano group, a $C_2$-$C_{12}$ linear, $C_3$-$C_{12}$ branched or $C_3$-$C_{12}$ cyclic alkyl group or a $C_6$-$C_{12}$ aryl group.

With regard to $R^{20}$, concrete examples of the $C_2$-$C_{12}$ linear alkyl group are ethyl group, n-propyl group, n-butyl group, n-pentyl group, n-hexyl group, n-heptyl group, n-octyl group, n-nonyl group, n-decyl group and n-dodecyl group.

A concrete structure of the $C_3$-$C_{12}$ branched or $C_3$-$C_{12}$ cyclic alkyl is identical to $R^9$ to $R^{15}$ of the general formulas (7) and (8).

In the alkyl group or the aryl group, each of some or all of hydrogen atoms may be substituted with a fluorine atom, a chlorine atom, a bromine atom or an iodine atom and each of some of carbon atoms may be substituted with a sulfur atom and a carbonyl group or a sulfonyl group may be contained.

"n" is any integer between 0 and 2 and "p" is any integer between 1 and 5. If the number of $R^{11}$ is two or more, it is not inquired whether l and m are identical or different.

In the general formula (12), Y represents a single bond or a $C_1$-$C_4$ linear, $C_3$-$C_4$ branched or $C_3$-$C_4$ cyclic alkylene group.

With regard to Y, concrete examples of the $C_1$-$C_4$ linear, $C_3$-$C_4$ branched or $C_3$-$C_4$ cyclic alkylene group are methylene group, ethylene group, n-propylene group, i-propylene group, n-butylene group, cyclopropylene group and cyclobutylene group.

In the alkylene group, each of some or all of hydrogen atoms may be substituted with a fluorine atom, a chlorine atom, a bromine atom or an iodine atom and an ether bond or an ester bond may be contained.

In the general formula (12), M represents an alkali metal ion or an ammonium ion.

With regard to M, concrete examples of the alkali metal ion are lithium ion, sodium ion, potassium ion and cesium ion. Lithium ion, sodium ion and potassium ion are preferable.

With regard to M, concrete examples of the ammonium ion are methylammonium ion, ethylammonium ion, dimethylammonium ion, diethylammonium ion, trimethylammonium ion and triethylammonium ion. Diethylammonium ion, trimethylammonium ion and triethylammonium ion are preferable.

In the above-mentioned salt, a bis(perfluoroalkanesulfonyl)methyl anion has a low nucleophilicity. Consequently, the salt is difficult to cause reaction with a solvent or a solute, when used as an electrolyte. Moreover, the salt is soluble in a variety of organic solvents and therefore useful as a component of an electrolytic solution.

5. Solid Electrolyte Membrane Provided to Contain Polymer Comprising Repeating Unit Having Bis(perfluoroalkanesulfonyl)methyl Group A solid electrolyte membrane provided to include a polymer comprising a repeating unit having a bis(perfluoroalkanesulfonyl)methyl group, according to the present invention is as has been discussed in Invention 7.

5-1. Production of Polymer Comprising Repeating Unit Having Bis(perfluoroalkanesulfonyl)methyl Group A solid electrolyte membrane of the present invention is characterized by being provided to contain a polymer comprising a repeating unit having a bis(perfluoroalkanesulfonyl)methyl group and a norbornene skeleton, the repeating unit being represented by any one of the general formula (8-A), the general formula (8-B) and the general formula (8-C).

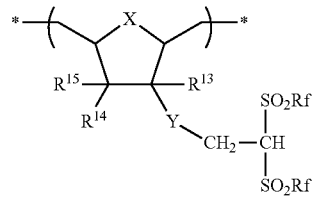

(8-A)

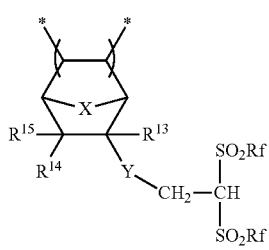

(8-B)

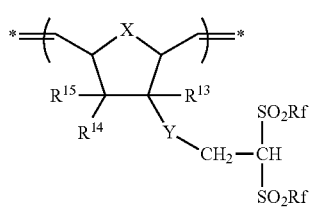

(8-C)

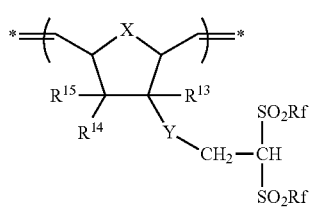

In the formula (8-A) to the formula (8-C), $R^{13}$ to $R^{15}$ mutually independently represent a hydrogen atom or a $C_1$-$C_{12}$ linear, $C_3$-$C_{12}$ branched or $C_3$-$C_{12}$ cyclic alkyl group or a $C_6$-$C_{12}$ aryl group.

Concrete examples of the $C_1$-$C_{12}$ linear, $C_3$-$C_{12}$ branched or $C_3$-$C_{12}$ cyclic alkyl group are methyl group, ethyl group, n-propyl group, i-propyl group, n-butyl group, t-butyl group, n-pentyl group, i-pentyl group, n-hexyl group, i-hexyl group, n-heptyl group, n-octyl group, i-octyl group, n-nonyl group, n-decyl group, n-dodecyl group, cyclopropyl group, cyclobutyl group, cyclopentyl group, cyclohexyl group, adamantylmethyl group and 2-norbornylmethyl group. Concrete examples of the $C_6$-$C_{12}$ aryl group are phenyl group, 1-naphthyl group, 2-naphthyl group, 1-anthryl group and 1-phenanthryl group. Methyl group, ethyl group, n-propyl group and phenyl group are preferable.

Additionally, in the alkyl group or the aryl group, each of some or all of hydrogen atoms may be substituted with a fluorine atom, a chlorine atom, a bromine atom or an iodine atom and an ether bond or an ester bond may be contained.

In the formula (8-A) to the formula (8-C), X represents $CH_2$, $C(CH_3)_2$ or an oxygen atom In the formula (8-A) to the formula (8-C), Y represents a single bond or a $C_1$-$C_4$ linear, $C_3$-$C_4$ branched or $C_3$-$C_4$ cyclic alkylene group.

With regard to Y, concrete examples of the $C_1$-$C_4$ linear, $C_3$-$C_4$ branched or $C_3$-$C_4$ cyclic alkylene group are methylene group, ethylene group, n-propylene group, i-propylene group, n-butylene group, cyclopropylene group and cyclobutylene group. Methylene group and ethylene group are preferable.

Furthermore, in the alkylene group, each of some or all of hydrogen atoms may be substituted with a fluorine atom, a chlorine atom, a bromine atom or an iodine atom and an ether bond or an ester bond may be contained.

A polymer comprising a repeating unit represented by the formula (8-A) to the formula (8-C) is a polymer obtained by polymerizing a polymerizable compound (15) represented by the general formula (15) and having a bis(perfluoroalkanesulfonyl)methyl moiety and a norbornene skeleton.

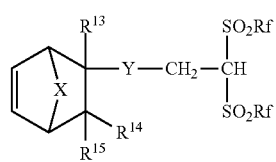

(15)

In the polymerizable compound (15), the definitions of $R_f$, $R^{13}$ to $R^{15}$, X and Y are identical to those of the formula (8-A) to the formula (8-C).

It is particularly preferable that the following polymerizable compound (BTSE-NB) is used for introducing a bis(perfluoroalkanesulfonyl)methyl moiety and a norbornene skeleton into the polymer.

BTSE-NM, which is synthesized from a commercially available 2-norbornenecarboxaldehyde as shown in the following reaction formula, is a raw material compound suitable for obtaining a solid electrolyte membrane of the present invention.

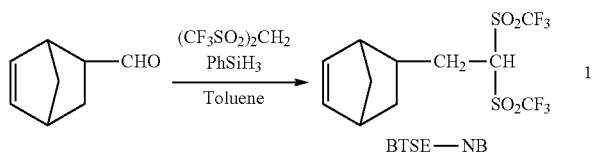

Then, polymerization reaction of a polymerizable compound (15) will be discussed.

A polymerization method for obtaining a polymer from a polymerizable compound (15) of the present invention is not particularly limited as far as it is a generally usable method; however, it is preferable that the method is radical polymerization or transition metal polymerization such as vinylene polymerization and ring-opening metathesis polymerization. It is possible to adopt ion polymerization, coordinate anionic polymerization, living anionic polymerization or cationic polymerization.

As a polymerization method for obtaining a polymer from a polymerizable compound (15) of the present invention, it is particularly preferable to produce the polymer according to the following reaction formula.

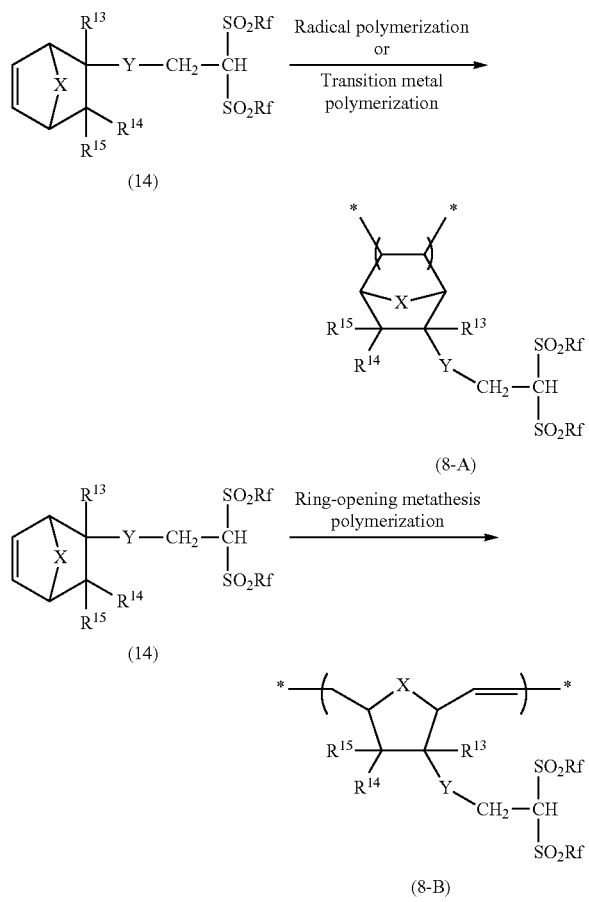

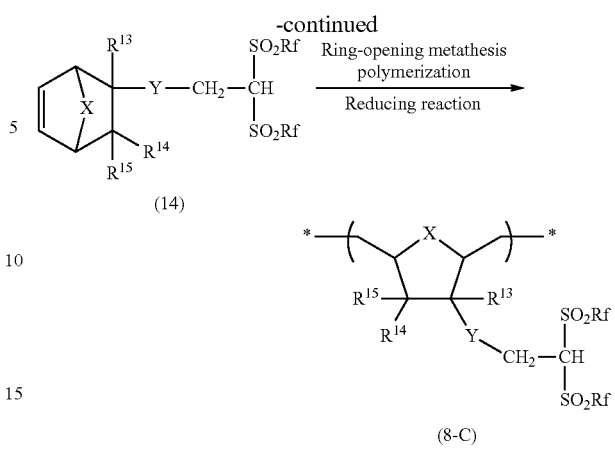

(In the formula, an asterisk "*" represents a bonding hand.)

First of all, radical polymerization will be described.

Radical polymerization is performed through an operation selected from a batch-wise operation, semi-continuous operation and continuous operation in the presence of a radical polymerization initiator or radial polymerization initiating source, according to a publically known polymerization method selected from bulk polymerization, solution polymerization, suspension polymerization and emulsion polymerization.

The radical polymerization initiator is not particularly limited, but concretely exemplified by azo-based compounds, peroxide-based compounds and redox-based compounds. In the case of producing a polymer comprising a repeating unit represented by the general formula (8-A), it is preferable to use azobisisobutyronitrile, t-butyl peroxypivalate, di-tert-butyl peroxide, i-butyryl peroxide, lauroyl peroxide, succinic acid peroxide, dicinnamylperoxide, di-n-propylperoxydicarbonate, t-butylperoxyallyl monocarbonate, benzoyl peroxide, hydrogen peroxide or ammonium persulfate, for example. Azobisisobutyronitrile, t-butyl peroxypivalate, benzoyl peroxide and hydrogen peroxide are preferable.

In polymerization reaction for obtaining a polymer by using a polymerizable compound (15) of the present invention, a reactor to be used in polymerization reaction is not particularly limited. In the polymerization reaction, a polymerization solvent may be used. As the polymerization solvent to be used in the polymerization reaction for obtaining a resin that serves as an active component of solid electrolyte membrane of the present invention, one that does not interfere with radical polymerization is preferable. Concrete examples thereof are: ester-based solvents such as ethyl acetate and n-butyl acetate; ketone-based solvents such as acetone and methyl isobutyl ketone; hydrocarbon-based solvents such as toluene and cyclohexane; and alcohol-based solvents such as methanol, isopropyl alcohol and ethylene glycol monomethyl ether. Additionally, it is also possible to use water, an ether-based solvent, a cyclic ether-based solvent, a fluorohydrocarbon-based solvent or an aromatic solvent. These solvents may be used singly or in combination of not less than two kinds of them. Additionally, a molecular weight adjusting agent such as mercaptan may be used together therewith. In the polymerization reaction for obtaining a polymer contained in the solid electrolyte membrane of the present invention, the reaction temperature in a copolymerization reaction is suitably selected according to the radical polymerization initiator or radical polymerization initiating source, but preferably within a range of not lower than 20° C. and not higher than 200° C., more preferably within a range of not lower than 30° C. and not higher than 140° C.

Then, polymerization using a transition metal will be discussed.

Vinylene polymerization is required only to use a transition metal catalyst of the group VIII such as iron, nickel, rhodium, palladium, platinum and the like, or a metal catalyst of the groups IVB to VIB selected from zirconium, titanium, vanadium, chromium, molybdenum and tungsten in the presence of a co-catalyst, and to adopt a known method in the presence of a solvent. The polymerization catalyst is not particularly limited but, in the polymerization reaction for obtaining a resin represented by the general formula (8-A) of the present invention, it is particularly preferable to use: transition metal compounds of the group VIII, selected from iron(II) chloride, iron(III) chloride, iron (II) bromide, iron(III) bromide, iron(II) acetate, iron(III) acetylacetonate, ferrocene, nickelocene, nickel(II) acetate, nickel bromide, nickel chloride, dichlorohexylnickel acetate, nickel lactate, nickel oxide, nickel tetrafluoroborate, bis(allyl)nickel, bis(cyclopentadienyl)nickel, nickel(II) hexafluoroacetylacetonatetetrahydrate, nickel(II) trifluoroacetylacetonatedihydrate, nickel(II) acetylacetonatetetrahydrate, rho dium(III) chloride, rhodium tris(triphenylphosphine)trichloride, palladium(II) bis(trifluoroacetate), palladium (II) bis(acetylacetonate), palladium(II) 2-ethylhexanoate, palladium(II) bromide, palladium(II) chloride, palladium(II) iodide, palladium(II) oxide, monoacetonitriletris(triphenylphosphine)palladium(II) tretrafluoroborate, tetrakis(acetonitrile)palladium(II) tetrafluoroborate, dichlorobis(acetonitrile)palladium(II), dichlorobis(triphenylphosphine)palladium(II), dichlorobis(benzonitrile)palladium(II), palladium acetylacetonate, palladium bis(acetonitrile)dichloride, palladium bis(dimethylsulfoxide)dichloride and platinum bis(triethylphosphine)hydrobromide; and transition metal compounds of the groups IVB to VIB, selected from vanadium(IV) chloride, vanadium trisacetylacetonate, vanadium bisacetylacetonatedichloride, trimethoxy(pentamethylcyclopentadienyl)titanium(IV), bis(cyclopentadienyl) titanium dichloride and bis(cyclopentadienyl)zirconium dichloride. Iron(II) chloride, rhodium(III) chloride and palladium(II) chloride are preferable.

The amount of the catalyst is not lower than 0.001 mol % and not higher than 10 mol %, preferably not lower than 0.01 mol % and not higher than 1 mol % relative to the polymerizable compound to be used. The co-catalyst is exemplified by alkylaluminoxane and alkylaluminium. In the polymerization reaction for obtaining a resin represented by the general formula (8-A) of the present invention, it is possible to particularly cite: methylaluminoxane (MAO); trialkylaluminiums such as trimethylaluminium, triethylaluminium, tripropylaluminium, triisopropylaluminium, triisobutylaluminium, tri-2-methylbutylaluminium, tri-3-methylbutylaluminium, tri-2-methylpentylaluminium, tri-3-methylpentylaluminium, tri-4-methylpentylaluminium, tri-2-methylhexylaluminium, tri-3-methylhexylaluminium, trioctylaluminium and the like; dialkylaluminium halides selected from dimethylaluminium chloride, diethylaluminium chloride, diisopropylaluminium chloride and diisobutylaluminium chloride; monoalkylaluminium halides selected from methylaluminium dichloride, ethylaluminium dichloride, ethylaluminium diiodide, propylaluminium dichloride, isopropylaluminium dichloride, butylaluminium dichloride and isobutylaluminium dichloride; and alkylaluminium sesquichlorides selected from methylaluminium sesquichloride, ethylaluminium sesquichloride, propylaluminium sesquichloride and isobutylaluminium sesquichloride. Trimethylaluminium, triisopropylaluminium and dimethylaluminium chloride are preferable.

In the case of methylaluminoxane, the amount of the co-catalyst is not lower than 50 equivalents and not higher than 500 equivalents in terms of Al conversion. In the case of other alkylaluminiums, the amount of the co-catalyst is within a range of 100 equivalents or less, preferably 30 equivalents or less by molar ratio relative to the transition metal catalyst. Additionally, the polymerization solvent is required only not to interfere with the polymerization reaction, and representative examples thereof are aromatic hydrocarbon-based ones selected from benzene, toluene, xylene, chlorobenzene and dichlorobenzene, hydrocarbon-based ones selected from hexane, heptane and cyclohexane, halogenated hydrocarbon-based ones selected from carbon tetrachloride, chloroform, methylene chloride and 1,2-dichloroethane, dimethylformamide, N-methylpyrolidone and N-cyclohexylpyrolidone. Toluene, heptane and chloroform are preferable.

These polymerization solvents may be used singly or in combination of two or more kinds. The reaction temperature is preferably not lower than −70° C. and not higher than 200° C. in general, particularly preferably not lower than −40° C. and not higher than 80° C.

Ring-opening metathesis polymerization is required only to use a transition metal catalyst of the group IV, V, VI or VII in the presence of a co-catalyst and to use a known method in the presence of a solvent. The transition metal catalyst is not particularly limited and exemplified by Ti-based, V-based, Mo-based and W-based catalysts. In particular, titanium(IV) chloride, vanadium(IV) chloride, vanadium trisacetylacetonate, vanadium bisacetylacetonatedichloride, molybdenum(VI) chloride and tungsten(VI) chloride are preferable in the polymerization reaction for obtaining a resin represented by the general formulas (8-B) and (8-C) of the present invention. The amount of the catalyst is not lower than 0.001 mol % and not higher than 10 mol %, preferably not lower than 0.01 mol % and not higher than 1 mol % relative to ad monomer to be used.

As a co-catalyst, it is possible to cite alkylaluminium and alkyltin. In particular, it is possible to cite: aluminium-based ones represented by trialkylaluminiums selected from trimethylaluminium, triethylaluminium, tripropylaluminium, triisopropylaluminium, triisobutylaluminium, tri-2-methylbutylaluminium, tri-3-methylbutylaluminium, tri-2-methylpentylaluminium, tri-3-methylpentylaluminium, tri-4-methylpentylaluminium, tri-2-methylhexylaluminium, tri-3-methylhexylaluminium and trioctylaluminium, dialkylaluminium halides selected from dimethylaluminium chloride, diethylaluminium chloride, diisopropylaluminium chloride and diisobutylaluminium chloride, monoalkylaluminium halides selected from methylaluminium dichloride, ethylaluminium dichloride, ethylaluminium diiodide, propylaluminium dichloride, isopropylaluminium dichloride, butylaluminium dichloride and isobutylaluminium dichloride, and alkylaluminium sesquichlorides selected from methylaluminium sesquichloride, ethylaluminium sesquichloride, propylaluminium sesquichloride and isobutylaluminium sesquichloride; tetra-n-butyltin; tetraphenyltin; and triphenylchlorotin. Triethylaluminium, triisopropylaluminium and tetra-n-butyltin are preferable.

The amount of the co-catalyst to be used is within a range of 100 equivalents or less, preferably 30 equivalents or less by molar ratio relative to the transition metal catalyst.

The polymerization solvent is required only not to interfere with the polymerization reaction, and representative examples thereof are aromatic hydrocarbon such as benzene, toluene, xylene, chlorobenzene and dichlorobenzene, hydrocarbon-based solvents such as hexane, heptane and cyclohexane, and halogenated hydrocarbons such as carbon tetrachloride, chloroform, methylene chloride and 1,2-dichloroethane. Toluene, heptane and chloroform are preferable.

In polymerization reaction for obtaining a resin represented by the general formulas (8-B) and (8-C) of the present invention, these polymerization solvents may be used singly or in combination of two or more kinds. The reaction temperature is preferably not lower than −70° C. and not higher than 200° C., more preferably not lower than −30° C. and not higher than 60° C.

5-2. Production of Solid Electrolyte Membrane

A powdery substance comprising a polymer obtained by the above-mentioned polymerization reaction is dissolved in an organic solvent such as 1,4-dioxane, acetone, tetrahydrofuran (THF), methyl ethyl ketone (MEK), methyl isobutyl ketone (MIBK), γ-butyrolactone, propylene glycol monoethyl ether acetate (PGMEA), polyethylene glycol monomethyl ether (PGME), ethyl lactate, dimethylformamide (DMF) and methanol as needed, and then applied onto a glass substrate or the like by a bar coater etc. Thereafter the solvent is volatilized, thereby producing a solid electrolyte membrane. The solid electrolyte membrane is immersed in an aqueous solution of hydrochloric acid or sulfuric acid as necessary, followed by being rinsed with ion exchange water. Preferable examples of the organic solvent are acetone, tetrahydrofuran and dimethylformamide.

Moreover, when impregnating a porous film with a solution containing the polymer, it is possible to add nano-silica particles, glass fibers and the like therein to enhance the mechanical strength of the solid electrolyte membrane. The thickness of the solid electrolyte membrane is not particularly limited but it is preferably not smaller than 10 μm and not larger than 200 μm. A thickness of smaller than 10 μm makes handling difficult, while a thickness of larger than 200 μm increases a membrane resistance so as to reduce the characteristics of an electrochemical device. The membrane thickness is adjusted by a thickness of application onto a substrate, i.e., by an application quantity per unit area.

6. Membrane Electrode Assembly, Polymer Electrolyte Fuel Cell and Direct Methanol Fuel Cell, Using Solid Electrolyte Membrane The present invention involves Inventions 8 to 10.

In the present invention, a membrane electrode assembly is obtained by disposing a pair of electrodes in a manner to sandwich a solid electrolyte membrane of Invention 7 therebetween.

When using the membrane electrode assembly according to the present invention as an electrical power generation element for a polymer electrolyte fuel cell or particularly for a direct methanol fuel cell, a solid electrolyte membrane of Invention 7 exhibits a great proton conductivity while suppressing methanol permeation. With this, electrical power generation is developed with efficiency, so that the amount of electrical power generation is increased by an increase of methanol concentration or a fuel tank can be reduced in size. Furthermore, an electrical power generation-controlling part provided to the membrane electrode assembly can be simplified so that a downsizing of a device can easily be attained.

EXAMPLES

Hereinafter, the present invention will more specifically be explained with reference to Examples; however, the present invention is not limited to those Examples. Incidentally, methyl group (—CH$_3$) and trifuryl group (—SO$_2$CF$_3$) may hereinafter be abbreviated as Me and Tf, respectively. Moreover, the yield of the target compound was determined by NMR yield obtained from areal percentage in a NMR chart.

To begin with, a method for producing a compound (5) having a bis(perfluoroalkanesulfonyl)methyl group will concretely be discussed with reference to Examples 1 to 8.

Example 1

Production of Bis(trifluoromethanesulfonyl)heptane Using Phenylsilane as a Reducing Agent The reaction formula of this production method is shown below.

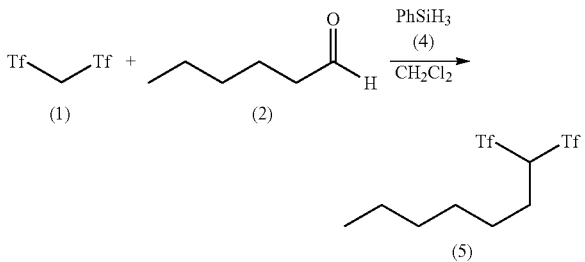

Hexanal in an amount of 1.1 g was dissolved in 10 ml of dichloromethane. Then, 2.8 g of bis(trifluoromethanesulfonyl)methane was added thereto as a compound (1) of Invention 1, followed by stirring for 15 minutes at room temperature. Thereafter, 1.1 g of phenylsilane as a compound (4) and as a reducing agent was added thereto and stirred for 14 hours at room temperature. Magnesium sulfate in an amount of 1.0 g was added to a reaction liquid obtained after stirring, and then dehydration and drying were performed, followed by conducting filtration. A filtrate was concentrated under a reduced pressure, and then purified by distillation under a condition that the temperature was 90° C. and the pressure was 1.33 Pa, thereby obtaining 2.7 g of bis(trifluoromethanesulfonyl)heptane as a compound (5) with a yield of 75%. A result of nuclear magnetic resonance (NMR) measurement is shown below.

Colorless liquid: $^1$H NMR (400 MHz, CDCl$_3$): δ=0.90 (3H, t, J=7.1), 1.26-1.46 (6H, m), 1.67-1.77 (2H, m), 2.42-2.48 (2H, m), 4.79 (1H, t, J=5.61 Hz); $^{19}$F NMR (376 Hz, CDCl$_3$): δ=−73.4 (6F, s)

Example 2

Production of Bis(trifluoromethanesulfonyl)heptane Using Phenyldimethylsilane as a Reducing Agent Phenyldimethylsilane having a high reducing property was used, instead of phenylsilane serving as a compound (4) of Example 1. The reaction formula of this production method is shown below.

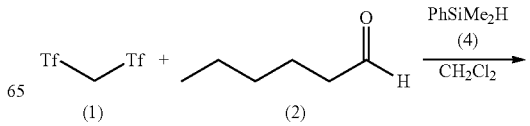

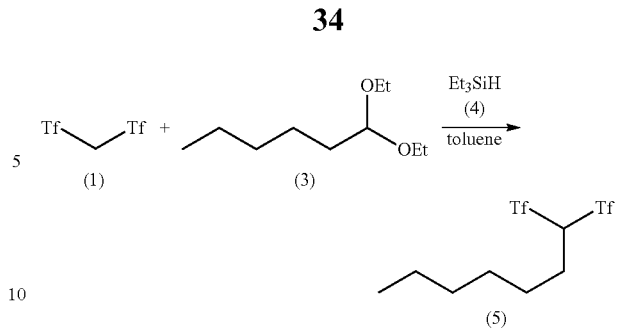

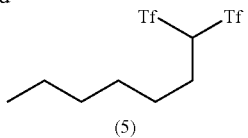

To a solution obtained from 1.1 g of hexanal and 10 ml of dichloromethane, 2.8 g of bis(trifluoromethanesulfonyl) methane was added as a compound (1) at room temperature, followed by stirring for 15 minutes. Thereafter, 1.5 g of phenyldimethylsilane as a compound (4) was added to the reaction solution and stirred for 14 hours at room temperature. A $^{19}$F-NMR measurement was conducted on the reaction solution in use of 151 mg of trifluoromethylbenezene as an internal standard substance, thereby obtaining bis(trifluoromethanesulfonyl)heptane as a compound (5) with a NMR yield of 32%.

In the case of using phenyldimethylsilane having a high reducing property instead of phenylsilane of Example 1, reduction of an aldehyde derivative was developed in advance so that the yield of a compound (5) was decreased.

Comparative Example 1

Production Though Catalytic Hydrogenation Using Palladium Carbon Catalyst in Hydrogen Atmosphere Reduction was carried out in a hydrogen atmosphere by using a palladium carbon catalyst instead of phenylsilane serving as a compound (4) of Example 1. The reaction formula is shown below.

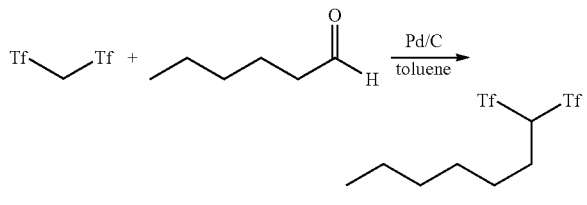

To a solution obtained from 280 mg of bis(trifluoromethanesulfonyl)methane and 1.0 ml of toluene, 100 mg of hexanal and 50 mg of a 5% palladium-carbon were added at room temperature, followed by stirring for 1 hour. A reaction solution was brought into a hydrogen atmosphere and stirred for 24 hours at room temperature. To the reaction solution, 151 mg of trifluoromethylbenezene as an internal standard substance was added, followed by conducting a $^{19}$F-NMR measurement. The reaction was complicated in the presence of the palladium catalyst, so that the NMR yield of bis (trifluoromethanesulfonyl)heptane, obtained from its ratio to the internal standard substance in terms of integrated value was decreased to 24%.

Example 3

Production of Bis(trifluoromethanesulfonyl)heptane Using an Acetal Compound

The reaction formula of this production method is shown below.

1,1-Diethoxyhexane in an amount of 174 mg as a compound (3) was dissolved in 1.0 ml of toluene. Then, 116 mg of triethylsilane as a compound (4) was added thereto as a reducing agent, followed by stirring for 15 minutes at room temperature. Thereafter, 280 mg of bis(trifluoromethanesulfonyl)methane as a compound (1) was added to the reaction solution and stirred for 12 hours at room temperature. After stirring, 95 mg of trifluoromethylbenezene as an internal standard substance was added to the reaction solution, followed by conducting a $^{19}$F-NMR measurement. The yield was calculated from the ratio to the internal standard substance in terms of integrated value, thereby obtaining a 75% yield of bis(trifluoromethanesulfonyl)heptane as a compound (5).

Example 4

Production of Bis(nonafluorobutanesulfonyl)heptane Using Triethylsilane as a Reducing Agent The reaction formula of this production method is shown below.

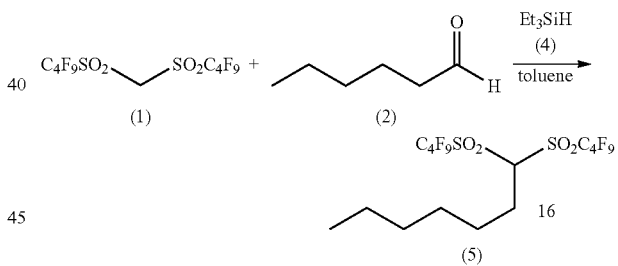

To a solution obtained from 290 mg of bis(nonafluorobutanesulfonyl)methane (as a compound (1)) and 1.0 ml of toluene, 55 mg of hexanal was added at room temperature, followed by stirring for 1 hour. Thereafter, 64 mg of triethylsilane as a compound (4) was added to the reaction solution and stirred for 30 hours at room temperature. Trifluoromethylbenzene in an amount of 151 mg as an internal standard substance was added to the reaction solution, followed by conducting a $^{19}$F-NMR measurement. The yield was calculated from the ratio to the internal standard substance in terms of integrated value, thereby obtaining a 86% NMR yield of bis(nonafluorobutanesulfonyl)heptane as a compound (5). A result of the NMR measurement is shown below.

$^1$H NMR (400 MHz, CDCl$_3$): δ=0.88 (3H, t, J=6.8 Hz), 1.18-1.42 (6H, m), 1.59-1.74 (2H, m), 2.35-2.48 (2H, m) 5.87 (1H, t, J=5.2 Hz); $^{19}$F NMR (376 Hz, CDCl$_3$): δ=−124.9-−126.0 (4F, m), −120.3 (2F, d, J=35.1 Hz), −105.9 (2F, brs), −80.2 (3F, t, J=9.2 Hz)

Example 5

Production of (2,2-bis(trifluoromethanesulfonyl)ethyl)cyclohexane Using Phenylsilane as a Reducing Agent The reaction formula of this production method is shown below.

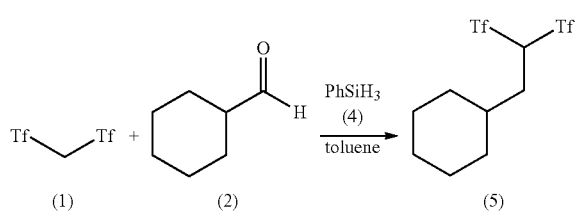

To a solution obtained from 280 mg of bis(trifluoromethanesulfonyl)methane, 54 mg of phenylsilane and 0.50 ml of toluene, a solution obtained from 168 mg of cyclohexanecarboxaldehyde and 0.5 ml of toluene was added throughout 30 minutes at room temperature. The reaction solution was stirred for 26 hours at room temperature, and then 176 mg of trifluoromethylbenzene as an internal standard substance was added thereto, followed by conducting a $^{19}$F-NMR measurement. The yield was calculated from the ratio to the internal standard substance in terms of integrated value, thereby obtaining a 99% NMR yield of (2,2-bis(trifluoromethanesulfonyl)ethyl)cyclohexane. A result of the NMR measurement is shown below.

$^1$H NMR (400 MHz, CDCl$_3$): δ=0.90-1.05 (1H, m), 1.10-1.42 (5H, m), 1.50-1.84 (5H, m), 2.28-2.46 (2H, m) 4.86 (1H, t, J=5.9 Hz); $^{19}$F NMR (376 Hz, CDCl$_3$): δ=−73.1 (6F, s)

Example 6

Production of 2-(2',2'-bis(trifluoromethanesulfonyl)ethyl)norbornene Using Phenylsilane as a Reducing Agent The reaction formula of this production method is shown below.

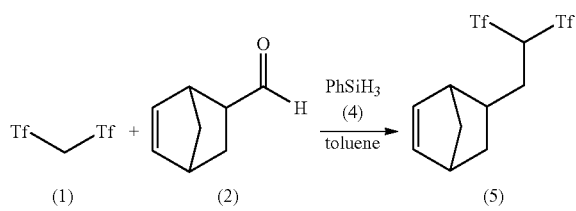

To a solution obtained from 1.5 g of bis(trifluoromethanesulfonyl)methane (as a compound (1)) and 6.0 ml of toluene, 0.95 g of 2-norbornenecarboxaldehyde (as a compound (2)) and 0.43 g of phenylsilane (as a compound (4)) were added at room temperature, followed by stirring for 18 hours. The reaction solution was concentrated under a reduced pressure and then purified by distillation, thereby obtaining 1.3 g of 2-(2',2'-bis(trifluoromethanesulfonyl)ethyl)norbornene as a compound (5) with a NMR yield of 66%. A result of the NMR measurement is shown below.

B.P. 98° C./4 mmHg; $^1$H NMR (400 MHz, CDCl$_3$): δ=0.68 (1H, ddd, 11.5, 4.4, 2.7 Hz), 1.30-1.37 (1H, m), 1.53 (1H, ddd, 8.1, 4.4, 2.0 Hz), 1.99 (1H, ddd, J=11.5, 8.1, 3.9 Hz), 2.14-2.24 (1H, m), 2.30-2.40 (1H, m), 2.46-2.57 (1H, m), 2.83-2.92 (2H, m), 4.77 (1H, t, J=6.1 Hz), 5.99 (1H, dd, 5.9, 2.8 Hz), 6.29 (1H, dd, 5.9, 3.1 Hz); $^{19}$F NMR (376 Hz, CDCl$_3$): δ=−72.88 (3F, s), −72.86 (3F, s)

Example 7

Production of (2,2-bis(trifluoromethanesulfonyl)ethyl)benzene Using Triethylsilane as a Reducing Agent The reaction formula of this production method is shown below.

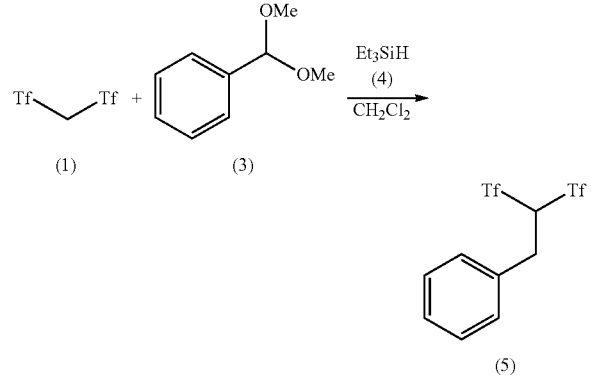

To a solution obtained from 280 mg of bis(trifluoromethanesulfonyl)methane (as a compound (1)) and 1.0 ml of dichloromethane, 152 mg of benzaldehyde dimethyl acetal (as a compound (3)) was added at room temperature and stirred for 1 hour. Triethylsilane in an amount of 116 mg (as a compound (4)) was added to the reaction solution to be reacted for 4 hours at room temperature. A 10 ml of saturated aqueous solution of sodium hydrogencarbonate was added to the reaction solution, followed by rinsing with 10 ml of isopropyl ether three times. A 15% hydrochloric acid in an amount of 20 ml was added to an aqueous phase to make it acidic, followed by performing extraction with 15 ml of isopropyl ether three times. Dehydration was carried out by using an anhydrous magnesium sulfate, and then an organic phase was subjected to filtration and concentration, thereby obtaining 300 mg of white crystals of (2,2-bis(trifluoromethanesulfonyl)ethyl)benzene with a yield of 81%. A result of a NMR measurement is shown below.

$^1$H NMR (400 MHz, CDCl$_3$): δ=3.79-3.90 (2H, m), 6.10 (1H, brs), 7.30-7.45 (5H, m); $^{19}$F NMR (376 Hz, CDCl$_3$): δ=−73.1 (6F, s)

Example 8

Production of 1-(2,2-bis(trifluoromethanesulfonyl)ethyl-2-fluorobenzene Using Triethylsilane as a Reducing Agent The reaction formula of this production method is shown below.

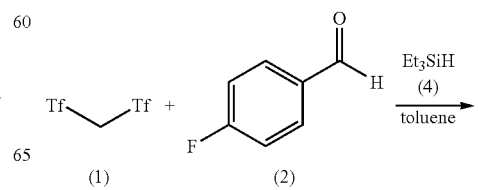

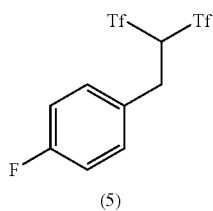

(5)

To a solution obtained from 124 mg of 4-fluorobenzaldehyde (as a compound (2)) and 1.0 ml of toluene, 280 mg of bis(trifluoromethanesulfonyl)methane (as a compound (1)) was added at room temperature and stirred for 30 minutes. Then, 116 mg of triethylsilane was added to the reaction solution and stirred for 17 hours at room temperature. To the reaction solution, 147 mg of trifluoromethylbenzene was added as an internal standard substance, followed by conducting a $^{19}$F-NMR measurement. The yield was calculated from the ratio to the internal standard substance in terms of integrated value, thereby obtaining a 69% NMR yield of 1-(2,2-bis(trifluoromethanesulfonyl)ethyl-2-fluorobenzene. A result of the NMR measurement is shown below.

$^1$H NMR (400 MHz, CDCl$_3$): δ=3.79 (2H, d, J=5.9 Hz), 4.96 (1H, t, 5.9 Hz), 7.03-7.12 (2H, m) 7.26-7.35 (2H, m); $^{19}$F NMR (376 Hz, CDCl$_3$): δ=−113.1 (1F, s), −73.0 (6F, s)

Example 9

Production of 1,4-bis(2,2-bis(trifluoromethanesulfonyl)ethyl)benzene Using Phenylsilane as a Reducing Agent The reaction formula of this production method is shown below.

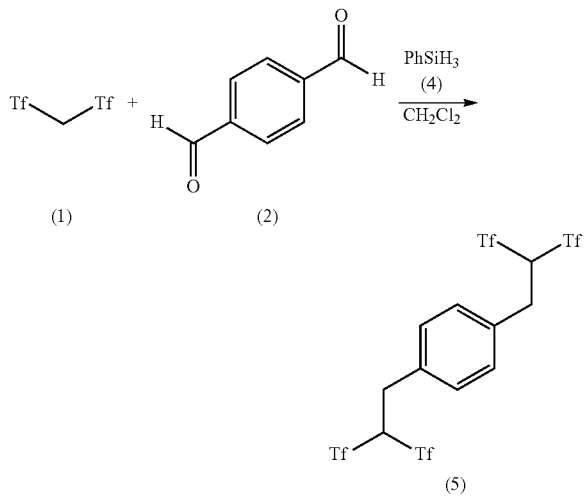

To a solution obtained from 134 mg of p-phthalaldehyde (as a compound (2)) and 1 ml of dichloromethane, 560 mg of bis(trifluoromethanesulfonyl)methane (as a compound (1)) was added at room temperature and then stirred for 2 hours. Phenylsilane (as a compound (4)) in an amount of 108 mg was added to the reaction solution and reacted for 1 week at room temperature. A 15% hydrochloric acid in an amount of 10 ml was added to the reaction solution, followed by performing extraction with 10 ml of isopropyl ether three times. An organic phase was mixed and then rinsed with 15 ml of water three times, and thereafter dehydrated by using an anhydrous magnesium sulfate. The organic phase was subjected to filtration and concentration, and residues were rinsed with 20 ml of toluene, thereby obtaining 324 mg of white crystals of 1,4-bis(2,2-bis(trifluoromethanesulfonyl)ethyl)benzene with a NMR yield of 47%. A result of a NMR measurement is shown below.

$^1$H NMR (400 MHz, CDCl$_3$): δ=3.81 (2H, d, J=5.4 Hz), 5.00 (1H, t, J=5.4 Hz), 7.35 (4H, s); $^{19}$F NMR (376 Hz, CDCl$_3$): δ=−73.1 (6F, s)

Referring now to Example 10, there will be discussed a method for producing an alkali metal salt having a bis(perfluoroalkanesulfonyl)methyl group.

Example 10

Production of a Salt Having a Bis(perfluoroalkanesulfonyl)methyl Group

The reaction formula of this production method is shown below.

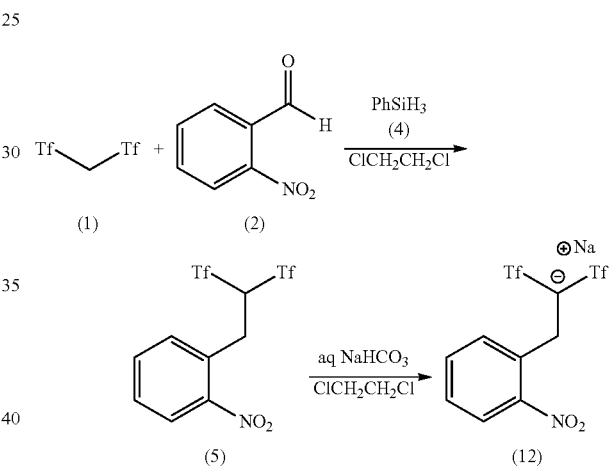

To a solution obtained from 1.5 g of 2-nitrobenzaldehyde (as a compound (2)) and 5 ml of 1,2-dichloroethane, 1.4 g of bis(trifluoromethanesulfonyl)methane (as a compound (1)) was added at room temperature, followed by conducting a heating reflux for 5 hours. Subsequently, 0.54 g of phenylsilane (as a compound (4)) was added to the reaction solution to be reacted under a heating reflux for 36 hours. After cooling to room temperature, 147 mg of trifluoromethylbenzene as an internal standard substance was added to the reaction solution, followed by conducting a $^{19}$F-NMR measurement. The yield was calculated from the ratio to the internal standard substance in terms of integrated value, thereby obtaining a 90% NMR yield of 1-(2,2-bis(trifluoromethanesulfonyl)ethyl-2-nitrobenzene. A result of the NMR measurement is shown below.

$^1$H NMR (400 MHz, CD$_3$CN): δ=4.05-4.14 (2H, m), 5.90 (1H, t, J=7.6 Hz); $^{19}$F NMR (376 Hz, CD$_3$CN): δ=−73.3 (6F, s)

A 20 ml of saturated aqueous solution of sodium hydrogencarbonate was added to the reaction solution and then an organic phase was separated. Thereafter, extraction was performed on an aqueous phase with 15 ml of isopropyl ether three times. After mixing the organic phase, dehydration was performed with the addition of magnesium sulfate, followed by conducting filtration and concentration. Residues were rinsed with 30 ml of toluene thereby obtaining 1.7 g of white crystals of a sodium salt of 1-(2,2-bis(trifluoromethanesulfonyl)ethyl-2-nitrobenzene (as a compound (12)) with a NMR yield of 78%. A result of the NMR measurement is shown below.

$^1$H NMR (400 MHz, CD$_3$CN): δ=3.73 (2H, brs), 7.13 (1H, t, J=7.5 Hz), 7.34-7.43 (1H, m), 7.54 (1H, d, J=7.8 Hz), 7.69 (1H, m); $^{19}$F NMR (376 Hz, CD$_3$CN): δ=−79.1 (6F, s)

A compound (12) can be used as an electrolyte having a bis(perfluoroalkanesulfonyl)methyl group.

Example 11

[Production of a Polymer Having a Repeating Unit Represented by the General Formula (8-A)]

As a production of a polymer using 2-(2',2'-bis(trifluoromethanesulfonyl)ethyl)norbornene, there was carried out a production of a polymer having a repeating unit represented by the general formula (8-A).

More specifically, productions of a polymer having a repeating unit represented by the general formula (8-A); a polymer having a repeating unit represented by the general formula (8-B); and a polymer having a repeating unit represented by the general formula (8-C) were carried out in use of 2-(2',2'-bis(trifluoromethanesulfonyl)ethyl)norbornene obtained in Example 6.

A solution of 2.1 mg of triphenylphosphine and 0.2 ml of toluene and a solution of 8.3 μl of boron trifluoride diethyl ether complex and 0.2 ml of toluene and a solution of 3.0 mg of dibenzylideneacetonepalladium and 0.2 ml of toluene were added to a solution obtained from 0.49 g of 2-(2',2'-bis(trifluoromethanesulfonyl)ethyl)norbornene (hereinafter, sometimes referred to as BTSE-NB) and 1.1 ml of 1,2-dichloroethane, and heated at 30° C. for 2 hours. The thus obtained reaction solution was poured into a large amount of n-heptane to cause reprecipitation of a polymer. The precipitated matter was separated from a solution by filtration to recover the polymer therefrom. The thus obtained polymer was subjected to a 4 hours of drying under a reduced pressure at 60° C. to remove a remaining solvent, thereby obtaining 0.15 g of a target polymer with a yield of 30%. Additionally, gel permeation chromatography (GPC) using polystyrene as a standard substance was conducted on the obtained polymer thereby determining its molecular weight. As a result, it was confirmed that the polymer had a number-average molecular weight (Mn) and a weight-average molecular weight (Mw) of 60,000 and 113,000, respectively, and a molecular weight distribution obtained therefrom (Mw/Mn) was 1.88.

Example 12

Production of a Polymer Having a Repeating Unit Represented by the General Formula (8-B)

To a solution obtained from 0.50 g of 2-(2',2'-bis(trifluoromethanesulfonyl)ethyl)norbornene (BTSE-NB) and 12 ml of toluene, 0.7 mg of (1,3-bis(2,4,6-trimethylphenyl)-2-imidazolidinylidene)dichloro(phenylmethylene)(trichlorohexylphosphine)ruthenium was added and then heated and refluxed for 1 hour. After distilling a solvent off, the obtained residual solution was poured into a large amount of n-heptane to cause reprecipitation of a polymer. The precipitated matter was separated from a solution by filtration to recover the polymer therefrom. The thus obtained polymer was subjected to a 4 hours of drying under a reduced pressure at 60° C. to remove a remaining solvent, thereby obtaining 0.44 g of a target polymer with a yield of 88%. Additionally, gel permeation chromatography (GPC) using polystyrene as a standard substance was conducted on the obtained polymer thereby determining its molecular weight. As a result, it was confirmed that the polymer had a number-average molecular weight (Mn) and a weight-average molecular weight (Mw) of 274,000 and 957,000, respectively, and a molecular weight distribution obtained therefrom (Mw/Mn) was 3.49.

Example 13

Production of a Polymer Having a Repeating Unit Represented by the General Formula (8-C)

A hydrogenation catalyst solution where 0.11 g of bis(tricyclohexylphosphine)benzylidyneruthenium(IV) chloride and 0.43 g of ethyl vinyl ether were dissolved in 4.3 ml of tetrahydrofuran was added to a solution obtained from 1.21 g of a ring-opened polymer (i.e. a polymer obtained in Example 12 and having a repeating unit represented by the general formula (8-B)) and 24 ml of tetrahydrofuran, followed by causing hydrogenation reaction at a hydrogen pressure of 3.0 MPa and a temperature of 100° C. for 4 hours. The hydrogenated reaction solution was poured into a large amount of n-pentane to precipitate a polymer out completely. After filtration and rinsing, a 5 hours of drying was performed under a reduced pressure at 80° C. thereby obtaining a ring-opened copolymer. Additionally, gel permeation chromatography (GPC) using polystyrene as a standard substance was conducted on the obtained polymer thereby determining its molecular weight. As a result, it was confirmed that the polymer had a number-average molecular weight (Mn) and a weight-average molecular weight (Mw) of 879,000 and 2,540,000, respectively, and a molecular weight distribution obtained therefrom (Mw/Mn) was 2.88.

Furthermore, a production of a solid electrolyte membrane was carried out in use of these polymers.

Example 14

Solid Electrolyte Membrane Production Example 1

A white solid in an amount of 0.05 g, which was obtained in Example 11 as a polymer having a repeating unit represented by the general formula (8-A), was dissolved in 0.1 g of N,N-dimethylformamide (hereinafter, sometimes referred to as DMF) and mixed. A polytetrafluoroethylene membrane having 83% porosity (available from Advantec Toyo Kaisha, Ltd. under the trade name of H100A) and cut out to have a size of 10×50 mm was disposed on a polyimide substrate and then the above-mentioned solution was applied thereto. The substrate was kept in a 25° C. oven for 4 hours. Thereafter, the temperature was increased at a rate of 1° C. per minute, and kept at 150° C. for 24 hours to cure the solution. Then, it was cooled to room temperature and immersed in water thereby obtaining an electrolyte membrane (Thickness: 0.05 mm, Size: 10 mm×50 mm) where a norbornene-based resin was supported on a polytetrafluoroethylene membrane having 83% porosity.

Example 15

Solid Electrolyte Membrane Production Example 2

A brown solid in an amount of 0.50 g, which was obtained in Example 12 as a polymer having a repeating unit represented by the general formula (8-B), was subjected to hot pressing in use of a hot press device at 170° C. and 10 MPa for 5 minutes, thereby obtaining a electrolyte membrane of a norbornene-based resin (Thickness: 31 μm, Size: 10 mm×50 mm).

Example 16

Solid Electrolyte Membrane Production Example 3

The procedures of Example 14 were repeated with the exception that a polymer having a repeating unit represented by the general formula (8-A) was replaced with a white solid obtained in Example 13 as a polymer having a repeating unit represented by the general formula (8-C) and that DMF was replaced with acetone, thereby obtaining a solid electrolyte membrane.

Comparative Example

A solid electrolyte membrane formed of a perfluorocarbon sulfonic acid-based polymer and available from Sigma-Aldrich Corporation under a trade name of Nafion No. 112 was dried under a heated condition of 150° C. for 24 hours.

[Proton Conductivity]

The proton conductivity of the solid electrolyte membranes of the present invention produced in Examples 14 and 15 and that of the solid electrolyte membrane of Comparative Example (Trade name: Nafion) were measured and the results were compared.

The proton conductivity was determined by the following procedure. A solid electrolyte membrane was cut out to have a size of 10 mm×50 mm and adhered to a platinum electrode disposed at 5 mm interval. An electrochemical impedance measurement device (model VFP 600 manufactured by Gamry Instruments Inc.) was connected to the electrode. Using this measurement device, the alternating-current resistance was determined by alternating-current impedance measurement within the frequency range of 1 Hz to 1 MHz. The specific resistance of the proton-conductive electrolyte membrane was calculated from the resistance gradient over the inter-electrode distance based on the following formula, and additionally, the alternating-current impedance was calculated from the inverse of the specific resistance. The calculation formulas of the specific resistance and the proton conductivity are indicated below.

Specific resistance $R$ (Ω·cm)=Membrane width (cm)×Membrane thickness (cm)×Resistance gradient between lines (Ω/cm)

Proton conductivity σ (S/cm)=1/$R$

On the solid electrolyte membranes obtained in Examples 14, 15 and 16 and Comparative Example, a measurement of the proton conductivity and a measurement of water content were conducted. Results are shown below.

TABLE 1

| | Amount of Acidic Group | Proton Conductivity | Water Content |
|---|---|---|---|
| Example 14 | 1.97 mmol/g | 5.0 × 10$^{-3}$ S/cm | 5 mass % |
| Example 15 | 2.49 mmol/g | 25.0 × 10$^{-3}$ S/cm | 25 mass % |
| Example 16 | 2.48 mmol/g | 61.0 × 10$^{-3}$ S/cm | 38 mass % |
| Comparative Example | 0.90 mmol/g | 5.0 × 10$^{-3}$ S/cm | 5 mass % |

The solid electrolyte membranes of Examples 14 to 16 were confirmed to have a good proton conductivity as compared with the solid electrolyte membrane of Comparative Example (available from Sigma-Aldrich Corporation under a trade name of Nafion).

As a result of subjecting the solid electrolyte membranes of Examples 14 to 16 of the present invention to a TG-DTA measurement, it was confirmed that a temperature at which the thermal decomposition was initiated was 250° C. and that any of these membranes were excellent in heat resistance.

[Methanol Permeability]

The methanol permeability was determined by the following procedure. The solid electrolyte membranes of Examples 14 to 16 were, after being immersed in ion exchange water for 1 day, sandwiched between separable type glass cells available from TechnoSigma Inc. One of the cells was charged with 20 ml of a mixed liquid of 10 mass % or 30 mass % methanol and water, whereas the other cell was charged with 20 ml of ion exchange water. Using a gas chromatograph (model GC2010 manufactured by Shimadzu Corporation), the concentration of methanol in the ion exchange water was measured with stirring at 25° C. As a result, methanol was not detected.

A solid electrolyte membrane of the present invention is excellent in heat resistance and has a proton conductivity, so as to be useful as a solid electrolyte membrane for a polymer electrolyte fuel cell and particularly for a direct methanol fuel cell.

The invention claimed is:

1. A method for producing a compound represented by general formula (5), comprising:
   initiating dehydration condensation between a compound represented by general formula (1) and an aldehyde compound represented by general formula (2) or an acetal compound represented by general formula (3); and then
   causing reduction with a hydrosilane compound represented by general formula (4);

(1)

(2)

(3)

(4)

(5)

wherein Rf represents a perfluoroalkyl group having 1 to 12 carbon atoms,

A represents a monovalent organic group,

Y represents a single bond or a substituted or unsubstituted $C_1$-$C_4$ linear alkylene group, a substituted or unsubstituted $C_3$-$C_4$ branched alkylene group, or a substituted or unsubstituted $C_3$-$C_4$ cyclic alkylene group, wherein one or more of the hydrogen atoms in any of the substituted $C_1$-$C_4$ linear alkylene group, substituted $C_3$-$C_4$ branched alkylene group, and substituted $C_3$-$C_4$ cyclic alkylene group is replaced by a fluorine atom, a chlorine atom, a bromine atom, or an iodine atom, and wherein any of the substituted $C_1$-$C_4$ linear alkylene group, substituted $C_3$-$C_4$ branched alkylene group, and substituted $C_3$-$C_4$ cyclic alkylene group comprises an ether bond or an ester bond;

$R^1$ and $R^2$ mutually independently represent a $C_1$-$C_{12}$ linear alkyl group, a $C_3$-$C_{12}$ branched alkyl group, or a $C_6$-$C_{12}$ cyclic alkyl group; and $R^3$ to $R^5$ mutually independently represent a hydrogen atom or a substituted or unsubstituted $C_1$-$C_8$ linear alkyl group, a substituted or unsubstituted $C_3$-$C_8$ branched alkyl group, a substituted or unsubstituted $C_6$-$C_8$ cyclic alkyl group, or a substituted or unsubstituted $C_6$-$C_8$ aryl group, wherein one or more of the hydrogen atoms in any of the substituted $C_1$-$C_8$ linear alkyl group, substituted $C_3$-$C_8$ branched alkyl group, substituted $C_6$-$C_8$ cyclic alkyl group, and substituted $C_6$-$C_8$ aryl group is replaced by a fluorine atom, a chlorine atom, a bromine atom, or an iodine atom, and wherein any of the substituted $C_1$-$C_8$ linear alkyl group, substituted $C_3$-$C_8$ branched alkyl group, substituted $C_6$-$C_8$ cyclic alkyl group and substituted $C_6$-$C_8$ aryl group comprises an ether bond or an ester bond.

2. A production method as claimed in claim 1, wherein the organic group A is a monovalent organic group represented by general formula (6), general formula (7), general formula (8) or general formula (9):

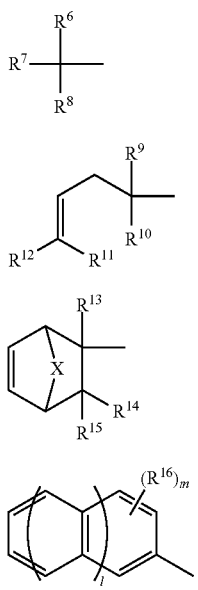

wherein $R^6$ to $R^{15}$ mutually independently represent a hydrogen atom or a substituted or unsubstituted $C_1$-$C_{12}$ linear alkyl group, a substituted or unsubstituted $C_3$-$C_{12}$ branched alkyl group, a substituted or unsubstituted $C_3$-$C_{12}$ cyclic alkyl group, or a substituted or unsubstituted $C_6$-$C_{12}$ aryl group, wherein one or more of the hydrogen atoms in any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group is replaced by a fluorine atom, a chlorine atom, a bromine atom, or an iodine atom, and wherein any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group comprises an ether bond or an ester bond, and $R^6$ to $R^8$ are bonded to form a cyclic structure;

X represents $CH_2$, $C(CH_3)_2$ or an oxygen atom;

$R^{16}$ mutually independently represents a hydrogen atom, a fluorine atom, a chlorine atom, a bromine atom, an iodine atom, a nitro group, a sulfonic acid group, a cyano group, a substituted or unsubstituted $C_1$-$C_{12}$ linear alkyl group, a substituted or unsubstituted $C_3$-$C_{12}$ branched alkyl group, a substituted or unsubstituted $C_3$-$C_{12}$ cyclic alkyl group, or a substituted or unsubstituted $C_6$-$C_{12}$ aryl group, wherein one or more of the hydrogen atoms in any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group is replaced by a fluorine atom, a chlorine atom, a bromine atom, or an iodine atom, and wherein any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group comprises an ether bond, an ester bond or a sulfonyl group;

l is an integer between 0 and 2; and m is an integer between 0 and 5.

3. A compound represented by general formula (5)

wherein A represents a monovalent organic group represented by general formula (8):

wherein $R^9$ to $R^{15}$ mutually independently represent a hydrogen atom or a substituted or unsubstituted $C_1$-$C_{12}$ linear alkyl group, a substituted or unsubstituted $C_3$-$C_{12}$ branched alkyl group, a substituted or unsubstituted $C_3$-$C_{12}$ cyclic alkyl group, or a substituted or unsubstituted $C_6$-$C_{12}$ aryl group, wherein one or more hydrogen atoms in any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group is replaced by a fluorine atom, a chlorine atom, a bromine atom, or an iodine atom, and wherein any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group comprises an ether bond or an ester bond;

X represents $CH_2$, $C(CH_3)_2$ or an oxygen atom;

Rf represents a perfluoroalkyl group having 1 to 12 carbon atoms, and

Y represents a single bond or a substituted or unsubstituted $C_1$-$C_4$ linear alkylene group, a substituted or unsubstituted $C_3$-$C_4$ branched alkylene group, or a substituted or unsubstituted $C_3$-$C_4$ cyclic alkylene group, wherein one or more of the hydrogen atoms in any of the substituted $C_1$-$C_4$ linear alkylene group, substituted $C_3$-$C_4$ branched alkylene group, and substituted $C_3$-$C_4$ cyclic alkylene group is replaced by a fluorine atom, a chlorine atom, a bromine atom, or an iodine atom, and wherein any of the substituted $C_1$-$C_4$ linear alkylene group, substituted $C_3$-$C_4$ branched alkylene group, and substituted $C_3$-$C_4$ cyclic alkylene group comprises an ether bond or an ester bond.

4. A method for producing a salt represented by general formula (12),

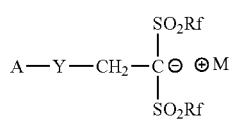

(12)

comprising:
(a) initiating dehydration condensation between a compound represented by general formula (1) and an aldehyde compound represented by general formula (2) or an acetal compound represented by general formula (3);
(b) causing reduction with a hydrosilane compound represented by general formula (4);

(1)

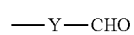

(2)

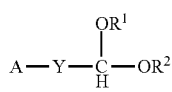

(3)

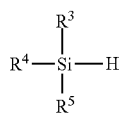

(4)

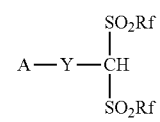

(5)

wherein Rf represents a perfluoroalkyl group having 1 to 12 carbon atoms,

A represents a monovalent organic group,

Y represents a single bond or a substituted or unsubstituted $C_1$-$C_4$ linear alkylene group, a substituted or unsubstituted $C_3$-$C_4$ branched alkylene group, or a substituted or unsubstituted $C_3$-$C_4$ cyclic alkylene group, wherein one or more of the hydrogen atoms in any of the substituted $C_1$-$C_4$ linear alkylene group, substituted $C_3$-$C_4$ branched alkylene group, and substituted $C_3$-$C_4$ cyclic alkylene group is replaced by a fluorine atom, a chlorine atom, a bromine atom, or an iodine atom, and wherein any of the substituted $C_1$-$C_4$ linear alkylene group, substituted $C_3$-$C_4$ branched alkylene group, and substituted $C_3$-$C_4$ cyclic alkylene group comprises an ether bond or an ester bond;

$R^1$ and $R^2$ mutually independently represent a $C_1$-$C_{12}$ linear alkyl group, a $C_3$-$C_{12}$ branched alkyl group, or a $C_6$-$C_{12}$ cyclic alkyl group; and $R^3$ to $R^5$ mutually independently represent a hydrogen atom or a substituted or unsubstituted $C_1$-$C_8$ linear alkyl group, a substituted or unsubstituted $C_3$-$C_8$ branched alkyl group, a substituted or unsubstituted $C_6$-$C_8$ cyclic alkyl group, or a substituted or unsubstituted $C_6$-$C_8$ aryl group, wherein one or more of the hydrogen atoms in any of the substituted $C_1$-$C_8$ linear alkyl group, substituted $C_3$-$C_8$ branched alkyl group, substituted $C_6$-$C_8$ cyclic alkyl group, and substituted $C_6$-$C_8$ aryl group is replaced by a fluorine atom, a chlorine atom, a bromine atom, or an iodine atom, and wherein any of the substituted $C_1$-$C_8$ linear alkyl group, substituted $C_3$-$C_8$ branched alkyl group, substituted $C_6$-$C_8$ cyclic alkyl group, and substituted $C_6$-$C_8$ aryl group comprises an ether bond or an ester bond; and (c) causing a neutralization reaction of a compound represented by general formula (5) with an alkali metal salt, wherein Rf represents a perfluoroalkyl group having 1 to 12 carbon atoms;

A represents a monovalent organic group;

Y represents a single bond or a substituted or unsubstituted $C_1$-$C_4$ linear alkylene group, a substituted or unsubstituted $C_3$-$C_4$ branched alkylene group, or a substituted or unsubstituted $C_3$-$C_4$ cyclic alkylene group, wherein one or more of the hydrogen atoms in any of the substituted $C_1$-$C_4$ linear alkylene group, substituted $C_3$-$C_4$ branched alkylene group, and substituted $C_3$-$C_4$ cyclic alkylene group is replaced by a fluorine atom, a chlorine atom, a bromine atom, or an iodine atom, and wherein any of the substituted $C_1$-$C_4$ linear alkylene group, substituted $C_3$-$C_4$ branched alkylene group, and substituted $C_3$-$C_4$ cyclic alkylene group comprises an ether bond or an ester bond; and M represents an alkali metal ion or an ammonium ion.

5. A method for producing a salt, as claimed in claim 4, wherein the organic group A is a monovalent organic group represented by general formula (6), general formula (7), general formula (8) or general formula (9):

(6)

-continued (7)

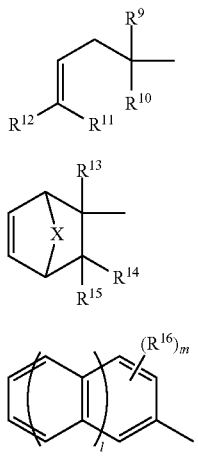

(8)

(9)

wherein $R^6$ to $R^{15}$ mutually independently represent a hydrogen atom or a substituted or unsubstituted $C_1$-$C_{12}$ linear alkyl group, a substituted or unsubstituted $C_3$-$C_{12}$ branched alkyl group, a substituted or unsubstituted $C_3$-$C_{12}$ cyclic alkyl group, or a substituted or unsubstituted $C_6$-$C_{12}$ aryl group, wherein one or more of the hydrogen atoms in any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group is replaced by a fluorine atom, a chlorine atom, a bromine atom, or an iodine atom, and wherein any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group comprises an ether bond or an ester bond; or $R^6$ to $R^8$ are bonded to form a cyclic structure;

X represents $CH_2$, $C(CH_3)_2$ or an oxygen atom;

$R^{16}$ mutually independently represents a hydrogen atom, a fluorine atom, a chlorine atom, a bromine atom, an iodine atom, a nitro group, a sulfonic acid group, a cyano group, a substituted or unsubstituted $C_1$-$C_{12}$ linear alkyl group, a substituted or unsubstituted $C_3$-$C_{12}$ branched alkyl group, a substituted or unsubstituted $C_3$-$C_{12}$ cyclic alkyl group, or a substituted or unsubstituted $C_6$-$C_{12}$ aryl group, wherein one or more of the hydrogen atoms in any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group is replaced by a fluorine atom, a chlorine atom, a bromine atom, or an iodine atom, and wherein any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group comprises an ether bond, an ester bond or a sulfonyl group;

l is an integer between 0 and 2; and m is an integer between 0 and 5.

6. A salt represented by general formula (12),

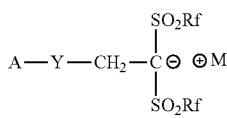

(12)

wherein A represents a monovalent organic group represented by general formula (8):

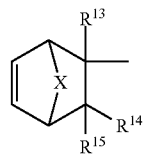

(8)

wherein $R^9$ to $R^{15}$ mutually independently represent a hydrogen atom or a substituted or unsubstituted $C_1$-$C_{12}$ linear alkyl group, a substituted or unsubstituted $C_3$-$C_{12}$ branched alkyl group, a substituted or unsubstituted $C_3$-$C_{12}$ cyclic alkyl group, or a substituted or unsubstituted $C_6$-$C_{12}$ aryl group, wherein one or more hydrogen atoms in any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group is replaced by a fluorine atom, a chlorine atom, a bromine atom, or an iodine atom, and wherein any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group comprises an ether bond or an ester bond;

X represents $CH_2$, $C(CH_3)_2$ or an oxygen atom;

Rf represents a perfluoroalkyl group having 1 to 12 carbon atoms;

Y represents a single bond or a substituted or unsubstituted $C_1$-$C_4$ linear alkylene group, a substituted or unsubstituted $C_3$-$C_4$ branched alkylene group, or a substituted or unsubstituted $C_3$-$C_4$ cyclic alkylene group, wherein one or more of the hydrogen atoms in any of the substituted $C_1$-$C_4$ linear alkylene group, substituted $C_3$-$C_4$ branched alkylene group, and substituted $C_3$-$C_4$ cyclic alkylene group is replaced by a fluorine atom, a chlorine atom, a bromine atom, or an iodine atom, and wherein any of the substituted $C_1$-$C_4$ linear alkylene group, substituted $C_3$-$C_4$ branched alkylene group, and substituted $C_3$-$C_4$ cyclic alkylene group comprises an ether bond or an ester bond; and M represents an alkali metal ion or an ammonium ion.

7. A polymer comprising a repeating unit having a bis (perfluoroalkanesulfonyl)methyl group and selected from the group consisting of general formula (8-A), general formula (8-B) and general formula (8-C):

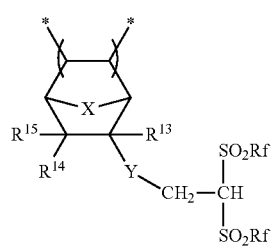

(8-A)

-continued

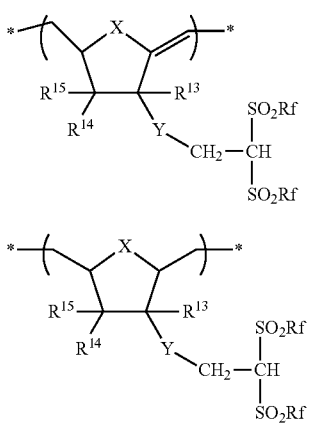

(8-B)

(8-C)

wherein Rf represents a perfluoroalkyl group having 1 to 12 carbon atoms, $R^{13}$ to $R^{15}$ mutually independently represent a hydrogen atom or a substituted or unsubstituted $C_1$-$C_{12}$ linear alkyl group, a substituted or unsubstituted $C_3$-$C_{12}$ branched alkyl group, a substituted or unsubstituted $C_3$-$C_{12}$ cyclic alkyl group, or a substituted or unsubstituted $C_6$-$C_{12}$ aryl group, wherein one or more hydrogen atoms in any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group is replaced by a fluorine atom, a chlorine atom, a bromine atom, or an iodine atom, and wherein any of the substituted $C_1$-$C_{12}$ linear alkyl group, substituted $C_3$-$C_{12}$ branched alkyl group, substituted $C_3$-$C_{12}$ cyclic alkyl group, and substituted $C_6$-$C_{12}$ aryl group comprises an ether bond or an ester bond, X represents $CH_2$, $C(CH_3)_2$ or an oxygen atom, Y represents a single bond or a substituted or unsubstituted $C_1$-$C_4$ linear alkylene group, a substituted or unsubstituted $C_3$-$C_4$ branched alkylene group, or a substituted or unsubstituted $C_3$-$C_4$ cyclic alkylene group, wherein one or more of the hydrogen atoms in any of the substituted $C_1$-$C_4$ linear alkylene group, substituted $C_3$-$C_4$ branched alkylene group, and substituted $C_3$-$C_4$ cyclic alkylene group is replaced by a fluorine atom, a chlorine atom, a bromine atom, or an iodine atom, and wherein any of the substituted $C_1$-$C_4$ linear alkylene group, substituted $C_3$-$C_4$ branched alkylene group, and substituted $C_3$-$C_4$ cyclic alkylene group comprises an ether bond or an ester bond; and an asterisk "*" represents a bonding hand.

8. A solid electrolyte membrane comprising a polymer as claimed in claim 7.

9. A membrane electrode assembly for fuel cells, comprising a solid electrolyte membrane as claimed in claim 8.

10. A polymer electrolyte fuel cell comprising a solid electrolyte membrane as claimed in claim 8.

11. A direct methanol fuel cell comprising a solid electrolyte membrane as claimed in claim 8.

* * * * *